(12) United States Patent
Kawajiri et al.

(10) Patent No.: US 12,224,060 B2
(45) Date of Patent: Feb. 11, 2025

(54) MODALITY CONTROLLING APPARATUS AND NON-VOLATILE COMPUTER-READABLE STORAGE MEDIUM STORING THEREIN DISPLAY CONTROLLING PROGRAM

(71) Applicant: CANON MEDICAL SYSTEMS CORPORATION, Otawara (JP)

(72) Inventors: Sho Kawajiri, Nasushiobara (JP); Kensuke Shinoda, Otawara (JP); Motohiro Miura, Yaita (JP); Masaaki Yamanaka, Otawara (JP); Shinya Ozawa, Nasushiobara (JP); Kazuya Tanoue, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 171 days.

(21) Appl. No.: 18/048,894

(22) Filed: Oct. 24, 2022

(65) Prior Publication Data

US 2023/0135113 A1 May 4, 2023

(30) Foreign Application Priority Data

Oct. 28, 2021 (JP) ................................. 2021-176493

(51) Int. Cl.
*G16H 40/67* (2018.01)
*H04N 7/18* (2006.01)

(52) U.S. Cl.
CPC ............. *G16H 40/67* (2018.01); *H04N 7/181* (2013.01); *H04N 7/188* (2013.01)

(58) Field of Classification Search
CPC . G06V 20/52; G06T 5/50; G06T 2207/20081; G06T 2207/20221; H04N 23/11
See application file for complete search history.

(56) References Cited

U.S. PATENT DOCUMENTS

| | | | |
|---|---|---|---|
| 10,387,612 B2* | 8/2019 | Wu ..................... | G16H 50/20 |
| 10,912,537 B2* | 2/2021 | Ng ..................... | A61B 6/037 |
| 2005/0228697 A1* | 10/2005 | Funahashi ............. | G16H 40/20 |
| | | | 705/2 |
| 2009/0213034 A1* | 8/2009 | Wu ....................... | G16H 50/20 |
| | | | 715/788 |
| 2011/0157154 A1* | 6/2011 | Bernard ............... | A61B 6/5229 |
| | | | 345/419 |
| 2012/0010475 A1* | 1/2012 | Rossmeier ............. | A61B 6/463 |
| | | | 600/301 |
| 2014/0292777 A1* | 10/2014 | Kudo .................... | G16H 40/63 |
| | | | 345/520 |

(Continued)

FOREIGN PATENT DOCUMENTS

JP 2014-188082 A 10/2014

*Primary Examiner* — Jared Walker
(74) *Attorney, Agent, or Firm* — Oblon, McClelland, Maier & Neustadt, L.L.P.

(57) ABSTRACT

A modality controlling apparatus according to an embodiment includes a display and a processing circuitry. The display is configured to display an input object for inputting an instruction for controlling a first modality and a status object indicating a status related to a second modality. The processing circuitry is configured to display the input object in a first section of the display and to display the status object in a second section of the display which is a section smaller than the first section.

14 Claims, 15 Drawing Sheets

(56) References Cited

U.S. PATENT DOCUMENTS

| | | | |
|---|---|---|---|
| 2015/0363054 A1* | 12/2015 | Sekiguchi | G06F 3/04883 |
| | | | 715/838 |
| 2017/0046482 A1* | 2/2017 | Kuo | G01R 33/546 |
| 2017/0236274 A1* | 8/2017 | Ishii | G16H 30/20 |
| | | | 382/115 |
| 2019/0171467 A1* | 6/2019 | Hermosillo Valadez | |
| | | | G06T 7/0012 |
| 2019/0223841 A1* | 7/2019 | Miyazawa | A61B 8/565 |
| 2020/0142553 A1* | 5/2020 | Ohtani | G06F 3/04886 |
| 2020/0303049 A1* | 9/2020 | Zhang | G06V 10/82 |
| 2020/0335198 A1* | 10/2020 | Accomazzi | G06T 7/0002 |
| 2021/0113161 A1* | 4/2021 | Fukushima | A61B 6/502 |
| 2021/0287783 A1* | 9/2021 | Jhaveri | G16H 80/00 |
| 2021/0304894 A1* | 9/2021 | Terai | G16H 30/20 |

\* cited by examiner

MODALITY CONTROLLING APPARATUS AND NON-VOLATILE COMPUTER-READABLE STORAGE MEDIUM STORING THEREIN DISPLAY CONTROLLING PROGRAM

CROSS-REFERENCE TO RELATED APPLICATIONS

This application is based upon and claims the benefit of priority from Japanese Patent Application No. 2021-176493, filed on Oct. 28, 2021, the entire contents of which are incorporated herein by reference.

FIELD

Embodiments described herein relate generally to a modality controlling apparatus and a non-volatile computer-readable storage medium storing therein a display controlling program.

BACKGROUND

Conventionally, for modalities such as magnetic resonance imaging apparatuses, X-ray computed tomography apparatuses, and X-ray diagnosis apparatuses, a console terminal configured to control each of these modalities is known. The console terminal is installed, for example, in an operation room near an examination room in which any of the modalities is installed. In recent years, besides the console terminal, a portable user interface terminal (e.g., a tablet) capable of operating each of a plurality of modalities has been used in some situations, as a terminal for controlling the modalities.

When using such a user interface terminal for operating a plurality of modalities in parallel, the user may find it difficult to understand which one of the modalities is currently being operated.

DETAILED DESCRIPTION

Figure 1:
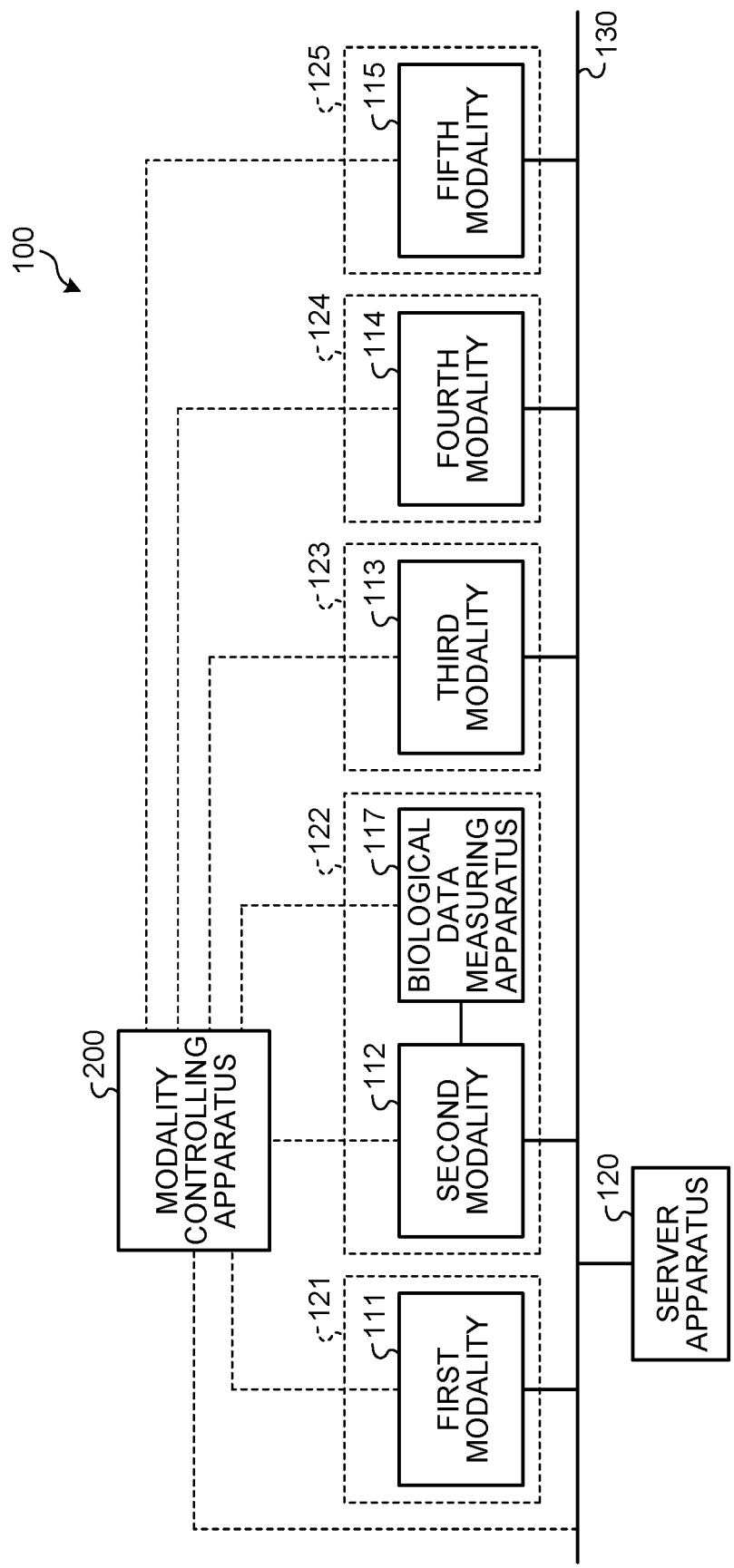
FIG. 1 is a block diagram illustrating an exemplary configuration of a medical image diagnosis system 100 according to an embodiment.

A modality controlling apparatus according to an embodiment includes a display and a processing circuitry. The display is configured to display an input object for inputting an instruction for controlling a first modality and a status object indicating a status related to a second modality. The processing circuitry is configured to display the input object in a first section of the display and to display the status object in a second section of the display which is a section smaller than the first section.

Exemplary embodiments of a modality controlling apparatus and a display controlling program will be explained in detail below, with reference to the accompanying drawings. For example, modalities correspond to various types of medical image diagnosis apparatuses such as an X-ray computed tomography apparatus (hereinafter, "X-ray CT apparatus"), an X-ray diagnosis apparatus, a magnetic resonance imaging apparatus (hereinafter, "MRI apparatus"), a nuclear medicine diagnosis apparatus, an ultrasound diagnosis apparatus, and/or the like. In the following embodiments, some of the constituent elements referred to by using the same reference characters are assumed to perform the same operations, and duplicate explanations thereof will be omitted, as appropriate.

EMBODIMENTS

FIG. 1 is a block diagram illustrating an exemplary configuration of a medical image diagnosis system 100 according to an embodiment. As illustrated in FIG. 1, the medical image diagnosis system 100 includes a plurality of modalities, a server apparatus 120, a biological data measuring apparatus 117 connected to a second modality, and a modality controlling apparatus 200. The plurality of modalities are five types of modalities, namely, a first modality 111, a second modality 112, a third modality 113, a fourth modality 114, and a fifth modality 115. The total number of the plurality of modalities does not necessarily have to be five. The present embodiment is applicable as long as there are two or more types of modalities.

The first to the fifth modalities are each a medical image diagnosis apparatus capable of communicating with the modality controlling apparatus 200. Each of the first to the fifth modalities is controlled by a console attached to the modality and by the modality controlling apparatus 200. The first to the fifth modalities are installed in first to fifth examination rooms, respectively. In the first to the fifth examination rooms, first to fifth cameras capable of imaging the first to the fifth modalities, respectively, may be installed. Each of the first to the fifth cameras may be installed on a gantry or the like of a corresponding one of the first to the fifth modalities.

As illustrated in FIG. 1, the first to the fifth modalities are connected to an intra-hospital Local Area Network (LAN) 130. As a result, the first to the fifth modalities are communicably connected to the server apparatus 120.

In the following sections, to explain a specific example, the first modality 111 is assumed to be an MRI apparatus of which a system ID related to identifying the modality is MR-1. The second modality 112 is assumed to be an MRI apparatus of which the system ID is MR-2. The third modality 113 is assumed to be an MRI apparatus of which the system ID is MR-3. The fourth modality 114 is assumed to be an X-ray CT apparatus of which the system ID is CT-1. The fifth modality 115 is assumed to be an X-ray CT apparatus of which the system ID is CT-2.

The biological data measuring apparatus 117 is configured to measure (acquire) biological data of an examined subject (hereinafter, "patient") undergoing a medical examination (hereinafter, "examination") in an examination room. FIG. 1 illustrates the biological data measuring apparatus 117 connected to the second modality 112 in a second examination room 122. The biological data measuring apparatus 117 may be connected to any other modality, depending on specifics of examinations to be performed on the patient. Examples of the biological data include an electrocardiogram waveform, the pulse, a blood flow, blood pressure, a skin temperature, an electroencephalogram, eyeball movements, a blood sugar value, a blood oxygen saturation level, and a respiratory waveform. The biological data measuring apparatus 117 is configured to acquire the biological data of the patient in a real-time manner and to transmit the acquired biological data to the second modality 112 connected to the biological data measuring apparatus 117. In this situation, the biological data measuring apparatus 117 may be a wearable apparatus which the patient is able to have on his/her body at all times. In that situation, as long as the patient has the wearable apparatus on his/her body, the wearable apparatus is able to obtain the biological data anywhere. The wearable apparatus is configured to transmit the biological data to the modality controlling apparatus 200.

For example, the server apparatus 120 is a server related to an information processing system in the medical institution such as a Radiology Information System (RIS), a Hospital Information System (HIS), or a Picture Archiving and Communication System (PACS). The server apparatus 120 is connected to the intra-hospital LAN 130. When the server apparatus 120 is an RIS server, the server apparatus 120 is configured to transmit appointment information (e.g., examination orders) about examinations related to the first to the fifth modalities, to the first to the fifth modalities, respectively. In addition, the server apparatus 120 is configured to transmit the appointment information about the examinations related to the first to the fifth modalities also to the modality controlling apparatus 200. When the server apparatus 120 is a PACS server, the PACS server is configured to store therein medical data acquired by the first to the fifth modalities.

For example, the modality controlling apparatus 200 is realized as a user interface terminal capable of communicating with the plurality of modalities and the server apparatus 120. Further, the modality controlling apparatus 200 may also be capable of communicating with the intra-hospital Local Area Network (LAN) 130, for example. More specifically, the user interface terminal is realized, for example, by using wireless hardware such as a tablet terminal or a smartphone held by a hospital worker such as a medical doctor or a medical technician.

Figure 2:
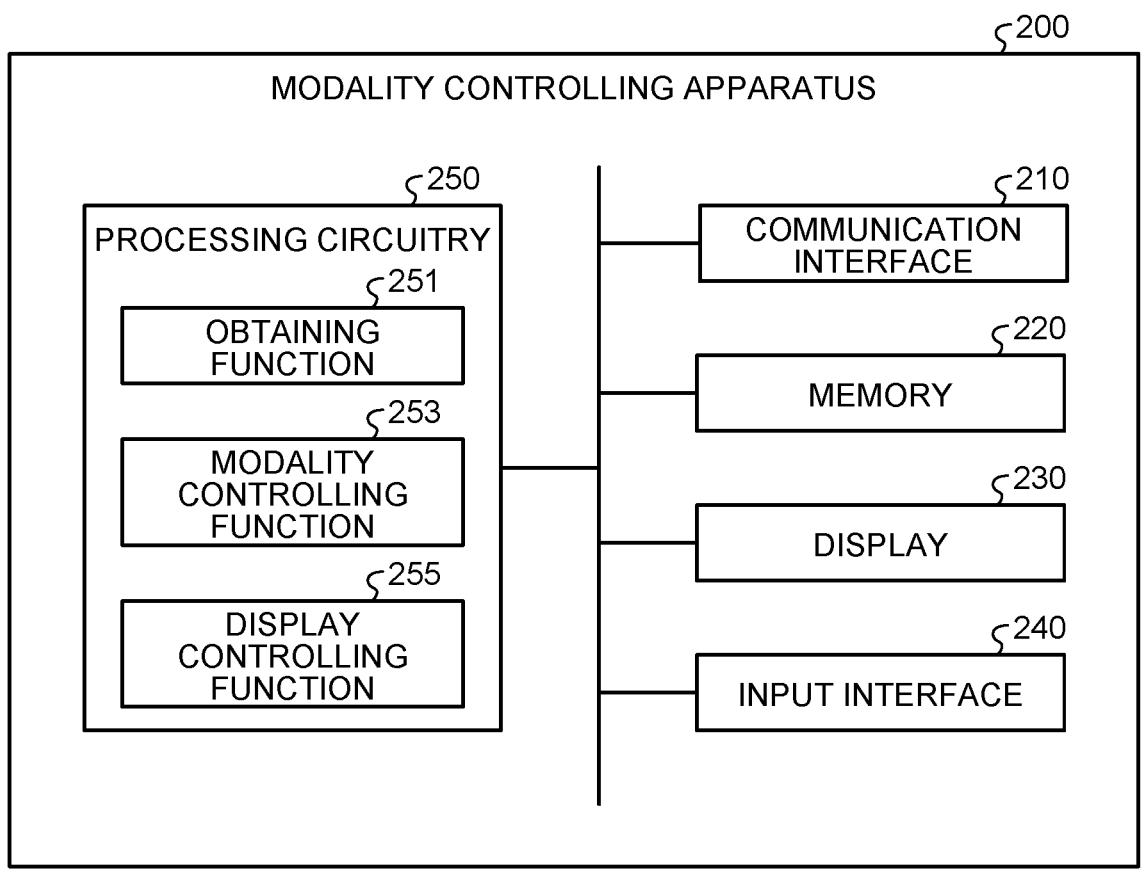
FIG. 2 is a block diagram illustrating an exemplary configuration of a modality controlling apparatus according to the embodiment.

FIG. 2 is a block diagram illustrating an exemplary configuration of the modality controlling apparatus 200. As illustrated in FIG. 2, the modality controlling apparatus 200 includes a communication interface 210, a memory 220, a display 230, an input interface 240, and a processing circuitry 250.

The communication interface 210 is configured to perform data communication with the server apparatus 120, each of the plurality of modalities, and the like connected via one or both of the intra-hospital LAN 130 and wireless communication. It is possible to use any standard as the standard for the communication with the server apparatus 120 and each of the plurality of modalities. It is possible to use, for example, an HL7 scheme, a Digital Imaging and Communications in Medicine (DICOM) scheme, or both. Further, when a camera is provided in any of the plurality of examination rooms in which the plurality of modalities are respectively installed, the communication interface 210 is configured to receive a picture taken by the camera. The communication interface 210 corresponds to a communication unit.

The memory 220 is configured to store therein various types of information. For example, as the memory 220, it is possible to use, as appropriate, a Hard Disk Drive (HDD), a Solid State Drive (SSD), or an integrated circuit storage apparatus. Alternatively, the memory 220 may be a Compact Disk Read-Only Memory (CD-ROM) drive, a Digital Versatile Disk (DVD) drive, or a drive apparatus configured to read and write various types of information from and to a portable storage medium such as a flash memory. For example, the memory 220 is configured to store therein examination information obtained from the server apparatus 120 realized with an RIS server or the like via the communication interface 210 and a user interface for controlling each of the plurality of modalities. Further, the memory 220 is configured to store therein various types of controlling programs related to the present embodiment and various types of data. Furthermore, the memory 220 is configured to store therein an input object for inputting instructions for controlling each of the plurality of modalities such as, for example, an input object for inputting an instruction for controlling the first modality 111. The memory 220 corresponds to a storage unit.

When an administrator who manages each of the plurality of modalities is set, the memory 220 is configured to store therein user IDs each set with a different one of the users in advance, so as to be kept in association with system IDs (hereinafter, "management IDs") of modalities (hereinafter, "managed modalities") managed by the users. For example, the memory 220 has stored therein a correspondence table (hereinafter, "managed modality correspondence table") such as a Look Up Table keeping the user IDs in association with the management IDs.

The display 230 is configured to display various types of information used by an operator for performing various tasks. For example, under control of a display controlling function 255 included in the processing circuitry 250, the display 230 is configured to display various types of Graphical User Interfaces (GUIs), a guidance screen for a medical technician, the input object for inputting an instruction for controlling each of the plurality of modalities, status objects each indicating a status of a different one of the plurality of modalities, and the like. For example, the display 230 is a display as a liquid crystal display monitor, but it is possible to use, as appropriate, any other arbitrary display known in the relevant technical field. In relation to the input object and the status objects, a GUI and display modes thereof on the display 230 will be explained later. The display 230 corresponds to a display unit.

The input interface 240 is configured to receive various types of instructions and inputs of information from the operator. For example, the input interface 240 is realized by using a switch button, a pointing device, a keyboard, a touchpad on which input operations can be performed by touching an operation surface displayed on the display 230, a touch screen in which a display screen and a touchpad are integrally formed, a contactless input circuitry using an optical sensor, an audio input circuitry, and/or the like. The input interface 240 is configured to receive operations from the user, for example. Examples of the operations performed by the user include an operation to move a mouse pointer, a click operation, a drag-and-drop operation, and operations to input instructions related to controlling each of the plurality of modalities. The input interface 240 is connected to the processing circuitry 250. The input interface 240 is configured to convert the input operations and the like received from the user into electrical signals and to output the electrical signals to the processing circuitry 250. The input interface 240 corresponds to an input unit.

The processing circuitry 250 includes, as hardware resources thereof, a processor and memory elements such as a Read-Only Memory (ROM) and a Random Access Memory (RAM) (not illustrated) and is configured to control the modality controlling apparatus 200. The processing circuitry 250 includes an obtaining function 251, a modality controlling function 253, and the display controlling function 255. Various types of functions implemented by the obtaining function 251, the modality controlling function 253, and the display controlling function 255 are stored in the memory 220 in the form of computer-executable programs. The processing circuitry 250 is a processor configured to realize the functions corresponding to the programs, by reading and executing the programs corresponding to the various types of functions from the memory 220. In other words, the processing circuitry 250 that has read the programs has, among others, the plurality of functions of the processing circuitry 250 illustrated in FIG. 2.

Although FIG. 2 illustrates the example in which the aforementioned various types of functions are realized by the single processing circuitry (i.e., the processing circuitry 250), it is also acceptable to realize the various types of functions as a result a plurality of independent processors executing the programs. In other words, the aforementioned various types of functions may be structured as the programs, so that the single processing circuitry executes the programs. Alternatively, one or more specific functions may be implemented in an dedicated independent program executing circuitry.

The aforementioned term "processor" denotes, for example, a Central Processing Unit (CPU), a Graphics Processing Unit (GPU), or a circuitry such as an Application Specific Integrated Circuit (ASIC) or a programmable logic device (e.g., a Simple Programmable Logic Device (SPLD), a Complex Programmable Logic Device (CPLD), or a Field Programmable Gate Array (FPGA)).

The processor in the processing circuitry 250 is configured to realize the various types of functions by reading and executing the programs saved in the memory 220. Alternatively, instead of having the programs saved in the memory 220, it is also acceptable to directly incorporate the programs in the circuitry of the processor. In that situation, the processor realizes the functions by reading and executing the programs incorporated in the circuitry thereof. Further, the obtaining function 251, the modality controlling function 253, and the display controlling function 255 are examples of an obtaining unit, a modality controlling unit, and a display controlling unit, respectively.

By employing the obtaining function 251, the processing circuitry 250 is configured to obtain the examination information from the server apparatus 120 realized with an RIS server or the like, via the communication interface 210. The examination information includes various types of information written in an examination order output from an HIS server to the RIS server, for example. The obtaining function 251 is configured to store the obtained examination information into the memory 220. Further, by employing the obtaining function 251, examination appointment information (hereinafter, "appointment status") of each of the plurality of modalities is obtained from the server apparatus 120 realized with an RIS server or the like, via the communication interface 210. The obtaining function 251 is configured to store the obtained appointment statuses into the memory 220.

In relation to the above, the appointment statuses may be generated by the modality controlling function 253 by chronologically arranging the examination information. In that situation, the obtaining function 251 does not need to obtain the appointment statuses. The obtaining function 251 is configured to obtain the biological data acquired by the biological data measuring apparatus 117. The obtaining function 251 is configured to store the obtained biological data into the memory 220 so as to be kept in association with the modalities.

From each of the plurality of modalities, the obtaining function 251 is configured to obtain status information indicating a status related to the modality via the communication interface 210. The obtaining function 251 is configured to store the obtained status information into the memory 220 so as to be kept in association with the system ID of the modality from which the status information was obtained. For example, the status indicated by the status information includes at least one of the following: a status of an imaging process performed by the modality; a status inside the examination room; a status of the patient; and a status of a worker or an administrator of the modality. For example, the status information includes at least one of the following: information indicating a state of an imaging process performed by at least one of the first to the fifth modalities; an examination room interior image related to at least one of the first to the fifth examination rooms in which the first to the fifth modalities are provided, respectively; environment information of at least one of the first to the fifth examination rooms; examined subject information of at least one of first to fifth patients imaged by the first to the fifth modalities; and administrator or worker information of the first to the fifth modalities.

Examples of the state of the imaging include: a total imaging period; an imaging period (hereinafter, "imaging execution period") from an imaging start time to the present time; an imaging remaining period, the ratio of the imaging execution period to the total imaging period; a standby state; a state of waiting for an instruction to start the imaging (waiting for the start of the imaging) during a patient setting process related to the imaging; the completion of the imaging; and occurrence of an error. For example, the examination room interior image may be an image (e.g., a monitoring image) taken by at least one camera (e.g., a monitoring camera) installed in the examination room and/or with the modality. The monitoring image includes at least the main body (e.g., the gantry) of the modality. In this situation, the monitoring image may be an image taken with specific timing or during a specific period such as while the patient and/or a medical technician are inside the examination room.

The environment information is temperature, humidity, and the like of the inside of the first to the fifth examination rooms (form 121 to 125). When an MRI apparatus is installed like in a first examination room 121 and the second examination room 122, the environment information may further include an oxygen concentration level inside the examination room. The environment information is obtained by various types of sensors installed in the first to the fifth examination rooms and/or with the first to the fifth modalities. The examined subject information corresponds to patient information (name, gender, age, height, weight, etc.) in the examination information obtained from the RIS, for example. Alternatively, the examined subject information may be obtained from the HIS server on the basis of the examination information. The administrators or the workers of the first to the fifth modalities each correspond to, for example, the name, an ID, a department to which he/she belongs, and the like regarding an administrator associated with the corresponding one of the first to the fifth modalities or a worker performing various tasks on the corresponding one of the first to the fifth modalities.

From each of the plurality of modalities, the obtaining function 251 is configured to obtain specifics of a task performed in relation to the modality and the time at which the specifics were carried out. Examples of the specifics of the tasks include: an operation of each of the plurality of modalities (e.g., tilting the gantry of an X-ray CT apparatus); opening and closing the door to each of the plurality of examination rooms; operations of a couch or a table and/or a couchtop and a tabletop; attaching and detaching an accessory component (e.g., a reception coil) to and from the modality in relation to the imaging; and an imaging preparation such as determining the position of the couchtop or the tabletop. The specifics of the tasks correspond to various types of events that are electrically detectable by using various types of sensors.

By employing the modality controlling function 253, the processing circuitry 250 is configured to control each of the plurality of modalities according to an instruction received from the user via the input interface 240. More specifically, according to specifics input to the input object, the modality controlling function 253 is configured to control the modality associated with the input object. More specifically, when a user instruction is input to the input object via the input interface 240, the modality controlling function 253 is configured to transmit the input user instruction, to the modality associated with the input object via the communication interface 210. As a result, the modality associated with the input object is controlled according to the specifics input to the input object.

By employing the display controlling function 255, the processing circuitry 250 is configured to control positional arrangements (layouts) and display modes of various types of objects displayed on the display 230. Examples of the objects include an icon and a tool bar, as well as a button, a slider, a progress bar, and the like on a screen and structure display/operation elements. The display controlling function 255 is configured to display the input object in a first section of the display 230. For example, the first section has an area equal to or larger than 50% of the display region of the display 230. In other words, the display controlling function 255 is configured to assign the first section to the area equal to or larger than 50% of the display region of the display 230.

For example, when the user ID matches the management ID of the first modality 111 at the time of a user logging into the modality controlling apparatus 200 or when the input object related to the first modality 111 is pre-configured to be displayed in the first section at the time of a log-in, the display controlling function 255 is configured to display, in the first section of the display 230, the input object for inputting an instruction for controlling the first modality 111. In other words, the display controlling function 255 is configured to display, in the first section, a console screen for one of the plurality of modalities. In response to an input operation performed on the input object displayed in the first section, the modality controlling function 253 is configured to control the modality corresponding to the console screen displayed in the first section so as to perform processes of setting image taking conditions, processing a captured image (image processing), and the like.

Further, the display controlling function 255 is configured to display, in a second section of the display 230 which is a section smaller than the first section, the status objects related to the plurality of modalities. The status objects have information indicating progress in the imaging processes by the plurality of modalities in the second section. In this situation, the display controlling function 255 is configured to change the status objects in the second section in accordance with the progress in the imaging processes performed by the plurality of modalities. For example, the display controlling function 255 is configured to express forms of the plurality of modalities controlled by the modality controlling apparatus 200 by using icons and to display, in the second section, the status objects including the plurality of icons corresponding to the plurality of modalities. In an example, the display controlling function 255 is configured, before the imaging, to cause the display 230 to display a monitoring image as a status object and configured, when the imaging is started, to change the display into a status object indicating a state of the imaging such as the ratio of an imaging execution period to a total imaging period. In that situation, the display controlling function 255 may be configured to cause the display 230 to display the monitoring image as a status object, when being triggered by the patient or a worker entering the imaging room prior to the imaging. In that situation, the display controlling function 255 may cause the display 230 to simply display, as a status object, text information reading "STAND BY" or the like, before the patient or the worker enters the imaging room. Further, the display controlling function 255 is configured to arrange the status objects in a row in the second section. When being unable to display the plurality of status objects corresponding to the plurality of modalities in the second section, the display controlling function 255 is configured to display, in the second section, the status object corresponding to each of the plurality of modalities, according to a scroll operation performed by the user via the input interface 240.

More specifically, the display controlling function 255 is configured to display, in the second section of the display 230, the plurality of status objects indicating the statuses related to the plurality of modalities including the first modality 111 and the second modality 112, by using display modes (e.g., hues, line types, etc.) corresponding to the plurality of modalities. The status objects have information about at least one of the following: the system ID corresponding to each of the plurality of modalities; the icons each corresponding to a different one of the plurality of modalities; a state of an imaging process; an examination room interior images; the environment information; the examined subject information; and an administrator or a worker. According to a selection made by the user, for example, the state objects are configured to include information having higher priority or higher necessity based on the user's custom preference, so as to fit the sizes of the state objects in the second section.

Further, the display controlling function 255 is configured to display, in a third section of the display 230 which is a section smaller than the first section, a first task history of tasks performed in the first section, by using display modes corresponding to the plurality of modalities. The first task history corresponds to a history of input operations performed on the input object in the first section, in the present modality controlling apparatus 200. For example, the display controlling function 255 is configured to display, in the third section, time stamps of the input operations performed in the first section and the specifics of the input operations performed in the first section at different points in time, as the first task history serving as a log of the input operations. For example, the third section is a region having a shape and a size that make it possible to display a plurality of lines of character strings by scrolling in the up-and-down directions and has a smaller area than the first section.

It is preferable to configure the first task history so that the status objects (e.g., the icons) displayed in the second section are kept in association with the logs related to the corresponding objects. For example, the display controlling function 255 is configured to display the first task history in the third section in such a manner that, with respect to each of the modalities, the frame of the icon in the second section is in the same color as the character string of the log in the first task history associated with the icon. With this arrangement, the display controlling function 255 is able to cause the display 230 to display the logs displayed in the third section so as to be kept in association with the system IDs displayed in the second section.

Further, the display controlling function 255 is configured to display, in a fourth section of the display 230 which is a section smaller than the first section, a second task history of tasks performed in relation to the plurality of modalities, by using display modes corresponding to the plurality of modalities. For example, the second task history corresponds to a history of specifics of the tasks performed in relation to the plurality of modalities. More specifically, similarly to the first task history displayed in the third section, the display controlling function 255 is configured to display, in the fourth section, time stamps of the tasks of the plurality of modalities and the tasks performed at different points in time by the plurality of modalities in the system, as the second task history serving as a log of the tasks. For example, the fourth section is a region having a shape and a size that make it possible to display a plurality of lines of character strings by scrolling in the up-and-down directions and, preferably, has a size equal to or similar to that of the third section.

The second task history indicates, for example, entry into and exit from the examination rooms, moving of the couch or the table including the couchtop or the tabletop; attaching and detaching an accessory component to and from the modality or the patient (e.g., when the modality is an MRI apparatus, attaching and detaching a reception coil, a synchronization unit such as the biological data measuring apparatus 117 used for synchronization with the imaging, etc.), the start of an imaging process, the completion of an imaging process, an operation to make a patient call such as a nurse call, and/or the like.

Similarly to the display in the third section, it is preferable to configure the second task history so that the status objects (e.g., the icons) displayed in the second section are kept in association with the logs of the tasks related to the corresponding objects. For example, the display controlling function 255 is configured to display the second task history in the fourth section in such a manner that, with respect to each of the modalities, the frame of the icon in the second section is in the same color as the character string of the log in the second task history associated with the icon. With this arrangement, the display controlling function 255 is able to cause the display 230 to display the logs displayed in the fourth section so as to be kept in association with the system IDs displayed in the second section.

Further, the display controlling function 255 is configured to display, in a fifth section of the display 230 which is a section smaller than the first section, the appointment statuses of the examinations to be performed by the plurality of modalities, by using display modes corresponding to the plurality of modalities. For example, the display controlling function 255 is configured to display, in the fifth section, the appointment statuses in descending order of priority levels of the appointments for the examinations. Examples of the information in the appointment statuses include: the system ID assigned to each of the plurality of modalities, the patient information, an outline of the imaging processes (e.g., the imaged body site, the presence/absence of contrast enhancement), and a time at which the imaging is scheduled. For example, the fifth section is a region having a shape and a size that make it possible to display a plurality of lines of character strings by scrolling in the up-and-down directions and, preferably, has a size equal to or similar to that of the third section.

Similarly to the display in the third section, it is preferable to configure the appointment statuses so that the status objects (e.g., the icons) displayed in the second section are kept in association with the appointment statuses. For example, the display controlling function 255 is configured to display the appointment statuses in the fifth section in such a manner that, with respect to each of the modalities, the frame of the icon in the second section is in the same color as the character string of the appointment associated with the icon. With this arrangement, the display controlling function 255 is able to cause the display 230 to display the logs displayed in the fifth section so as to be kept in association with the system IDs displayed in the second section.

Further, as for the positional arrangements of the first to the fifth sections on the display 230, the user may freely change the positional arrangements of the sections, as long as the first section satisfies the condition of being equal to or larger than the display region of the display 230, for example. Further, the display controlling function 255 may exercise the display control on at least one of the third to the fifth sections. In other words, whether the information is displayed or not in the third to the fifth sections and the positions of the first to the fifth sections may be customized as appropriate according to instructions received from the user via the input interface 240. Furthermore, the pieces of display information in the first to the fifth sections do not necessarily have to be completely separate. The display controlling function 255 may display the display information by combining or mixing the information together, as appropriate, according to modes of the display.

In response to an operation performed on any of the status objects, the display controlling function 255 is configured to display, in the first section, an authentication object for causing an input object related to the modality associated with the operated status object to be displayed in the first section. The authentication object may be, for example, an object for having the user confirm whether a pop-up display should be present or absent. For example, when the status object related to the second modality in the second section is designated by the user, the display controlling function 255 is configured to display, in the first section, an authentication object related to displaying the input object of the second modality 112 in the first section.

In this situation, the display controlling function 255 may display, in the second section, a visual effect such as lighting up the frame of the icon related to the modality being the target of the operation. Further, the display controlling function 255 may also display the system ID in the first section with the same or a similar visual effect. With these arrangements, the user is able to more intuitively recognize the modality currently being operated. In this situation, the visual effects may be kept permanently or may be restrictively used only for a number of seconds after the console screens are switched.

Figure 3:
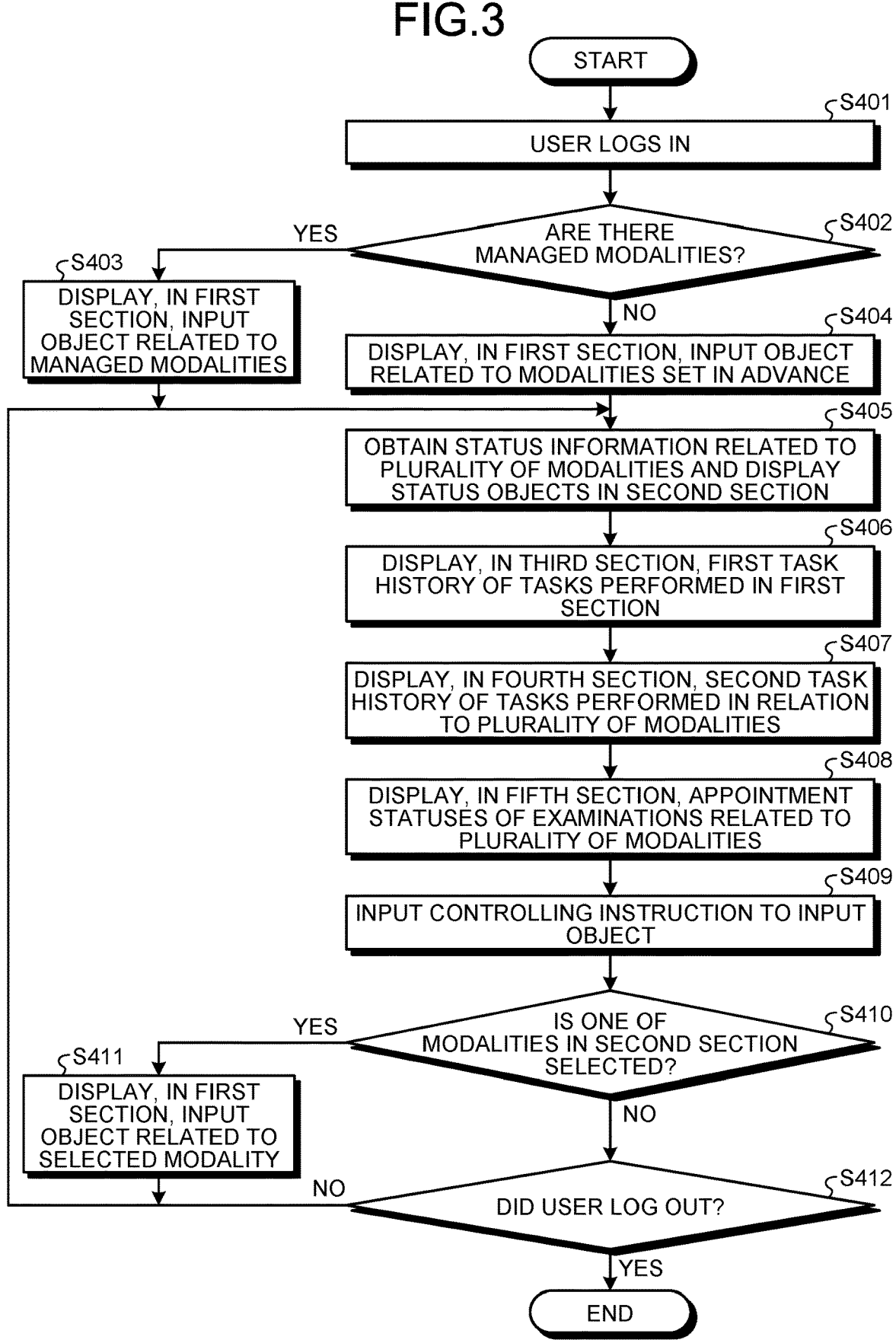
FIG. 3 is a flowchart illustrating an example of a flow in a display controlling process according to the embodiment.

A process of controlling the displays (hereinafter, "display controlling process") performed by the modality controlling apparatus 200 according to the present embodiment configured as described above will be explained with reference to FIGS. 3 to 8. To explain a specific example, it is assumed that the display region of the display 230 is divided into the first to the fifth sections. FIG. 3 is a flowchart illustrating an example of a flow in the display controlling process according to the embodiment.

The Display Controlling Process
Step S401:
The user logs into the present modality controlling apparatus 200. For example, the log-in is realized through fingerprint authentication, facial authentication, voice authentication, iris authentication, or the like. As a result, the processing circuitry 250 identifies the user ID of the user operating the modality controlling apparatus 200.
Step S402:
By employing the display controlling function 255, the processing circuitry 250 compares the identified user ID with the managed modality correspondence table. As a result of the comparison, when the identified user ID is present in the managed modality correspondence table (step S402: Yes), the process at step S403 will be performed. When the identified user ID is not present in the managed modality correspondence table (step S402: No), the process at step S404 will be performed.
Step S403:
The display controlling function 255 identifies a managed modality, by comparing the identified user ID with the managed modality correspondence table. Identifying the managed modality corresponds, in other words, to identifying the management ID. In the following sections, to explain a specific example, the identified managed modality is assumed to be the first modality 111. In other words, it is assumed that the identified management ID is MR-1. The obtaining function 251 obtains the examination information, the status information, and the like related to the modality having the management ID MR-1, from the first modality 111 and the server apparatus 120. For example, in response to the user's log-in, the display controlling function 255 displays, in the first section, the input object corresponding to the console screen for the first modality 111. Thus, the display 230 displays, in the first section, the input object for inputting an instruction for controlling the first modality 111.
Step S404:
The display controlling function 255 displays, in the first section, the input object related to a modality that is set in advance. Thus, the display 230 displays, in the first section, the input object for inputting an instruction for controlling the first modality 111. In the following sections, the modality that is set in advance is assumed to be the first modality 111. However, the modality that is set in advance does not necessarily need to be the first modality 111 and may be any other modality. For example, the modality that is set in advance may be a modality positioned closest to the modality controlling apparatus 200 or may be a modality that was operated by the modality controlling apparatus 200 before a log-out from the modality controlling apparatus 200.
Step S405:
The obtaining function 251 obtains the status information related to the plurality of modalities. The display controlling function 255 generates the status objects on the basis of the obtained status information. The display controlling function 255 displays, in the second section, the plurality of status objects related to the plurality of modalities, by using the display modes such as hues corresponding to the plurality of modalities. Thus, for example, the display 230 displays, in the second section, the status object indicating a status related to the second modality 112.
Step S406:
The obtaining function 251 obtains the first task history of tasks performed in the first section, from the plurality of modalities. The display controlling function 255 displays the obtained first task history in the third section by using the display modes such as hues corresponding to the plurality of modalities.
Step S407:
The obtaining function 251 obtains the second task history of the tasks performed in relation to the plurality of modalities, from the plurality of modalities. The display controlling function 255 displays the obtained second task history in the fourth section, by using the display modes such as hues corresponding to the plurality of modalities.
Step S408:
The obtaining function 251 obtains the appointment statuses of the examinations related to the plurality of modalities, either from the plurality of modalities or from the server apparatus 120 realized with an RIS server or the like. The display controlling function 255 displays the obtained appointment statuses of the examinations in the fifth section, by using the display modes such as hues corresponding to the plurality of modalities. The procedure in the processes at steps S402 through S408 does not necessarily have to be performed in the stated order.

Figure 4:
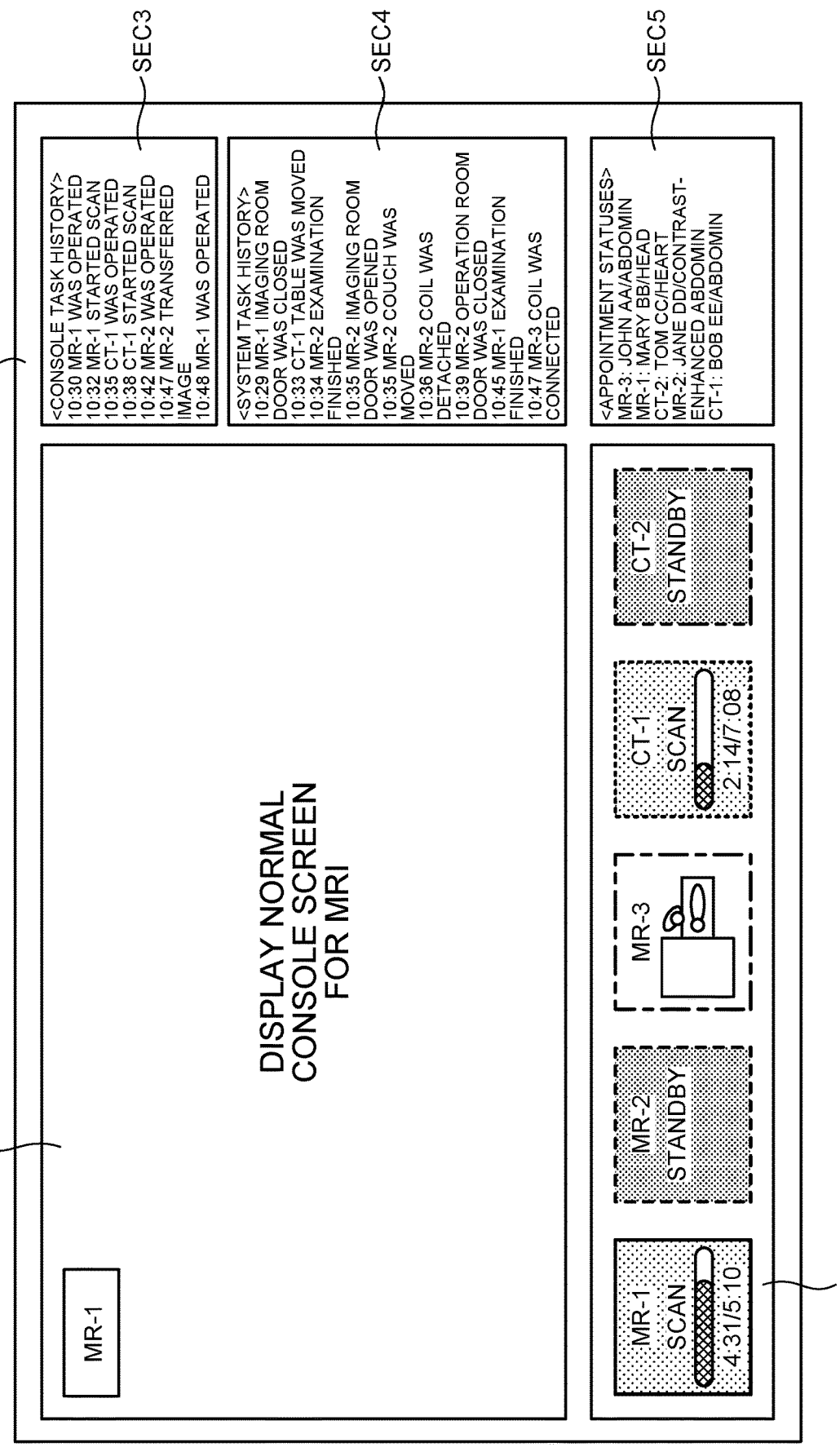
FIG. 4 is a drawing according to the embodiment illustrating an example of a display on a display.

FIG. 4 is a drawing illustrating an example of a display on the display 230 after step S408. As illustrated in FIG. 4, a display region DR of the display 230 is divided into the first to the fifth sections. As illustrated in FIG. 4, a first section SEC1 displays a console screen related to the first modality 111 of which the system ID is MR-1. Further, a second section SEC2 illustrated in FIG. 4 displays five status objects corresponding to the first to the fifth modalities. Each of the five status objects is displayed as being framed in a hue corresponding to the system ID. In the second section SEC2, the status of the first modality 111 of which the system ID is MR-1 is indicated by a status object being a progress bar that 4:31 (4 minutes and 31 seconds) has elapsed out of the scheduled imaging period of 5:10 (5 minutes and 10 seconds). In the first section SEC1 and the second section SEC2, the system ID "MR-1" of the first modality 111 is further displayed.

As illustrated in FIG. 4, in the second section SEC2, the status of the second modality 112 of which the system ID is MR-2 is indicated as being in a standby state. Further, in the second section SEC2, the status of the third modality 113 of which the system ID is MR-3 is displayed by a status object being a monitoring image indicating that the imaging process is in preparation. In the second section SEC2, the status of the fourth modality 114 of which the system ID is CT-1 is indicated by a status object being a progress bar that 2:14 (2 minutes and 14 seconds) has elapsed out of the scheduled imaging period of 7:08 (7 minutes and 08 seconds). Further, in the second section SEC2, the status of the fifth modality 115 of which the system ID is CT-2 is indicated as being in a standby state.

In the third section SEC3 illustrated in FIG. 4, a history (the first task history) of operations performed by the user in the first section SEC1 is displayed by using the hues corresponding to the first to the fifth modalities. In other words, the frame of each of the status objects in the second section SEC2 is displayed by using the same hue as that of the text in the first task history. Further, in the fourth section SEC4 illustrated in FIG. 4, a history (the second task history) of the tasks each related to a different one of the plurality of modalities is displayed by using the hues corresponding to the first to the fifth modalities. In other words, the frame of each of the status objects in the second section SEC2 is displayed by using the same hue as that of the text in the second task history. Further, in the fifth section SEC5 illustrated in FIG. 4, the appointment statuses each related to a different one of the plurality of modalities are displayed by using the hues corresponding to the first to the fifth modalities. In other words, the frame of each of the status objects in the second section SEC2 is displayed by using the same hue as that of the text in the second task history in the corresponding appointment status.

Figure 5:
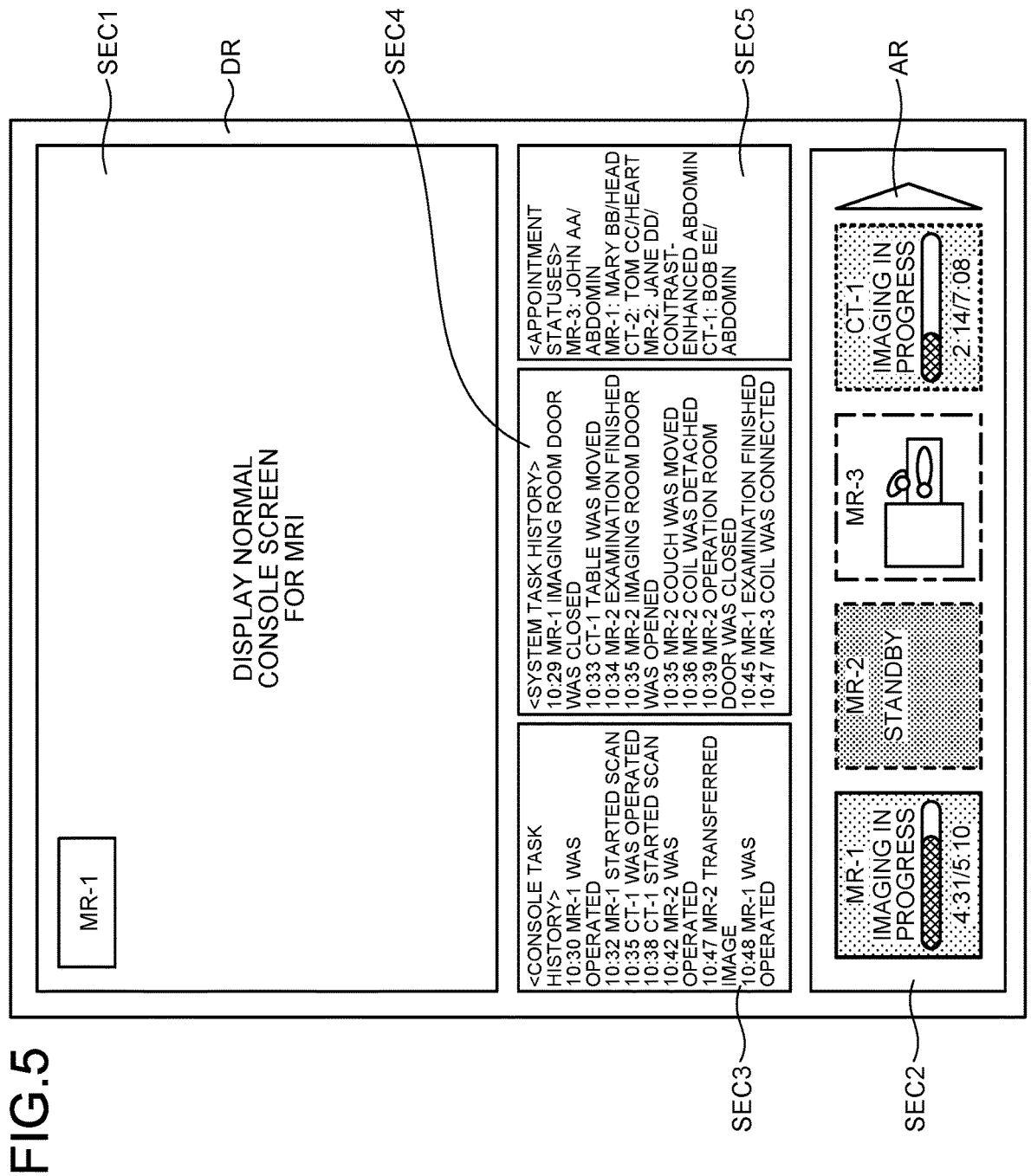
FIG. 5 is a drawing according to the embodiment illustrating an example of first to fifth sections in a display region in a portrait orientation, while the modality controlling apparatus is realized by using a tablet terminal.

FIG. 5 is a drawing illustrating an example of the first to the fifth sections in a display region in a portrait orientation, while the modality controlling apparatus 200 is realized by using a tablet terminal. When the orientation of the display 230 is changed from a landscape orientation to the portrait orientation as a result of the modality controlling apparatus 200 being rotated, the display layout of the first to the fifth sections is changed from the one in FIG. 4 to the one in FIG. 5, for example. In this situation, because the second section SEC2 is unable to display the status objects of all the modalities, the display controlling function 255 displays, in the second section SEC2, an arrow key (which may be referred to as a direction key) AR used for scrolling the status objects, as illustrated in FIG. 5.

Figure 6:
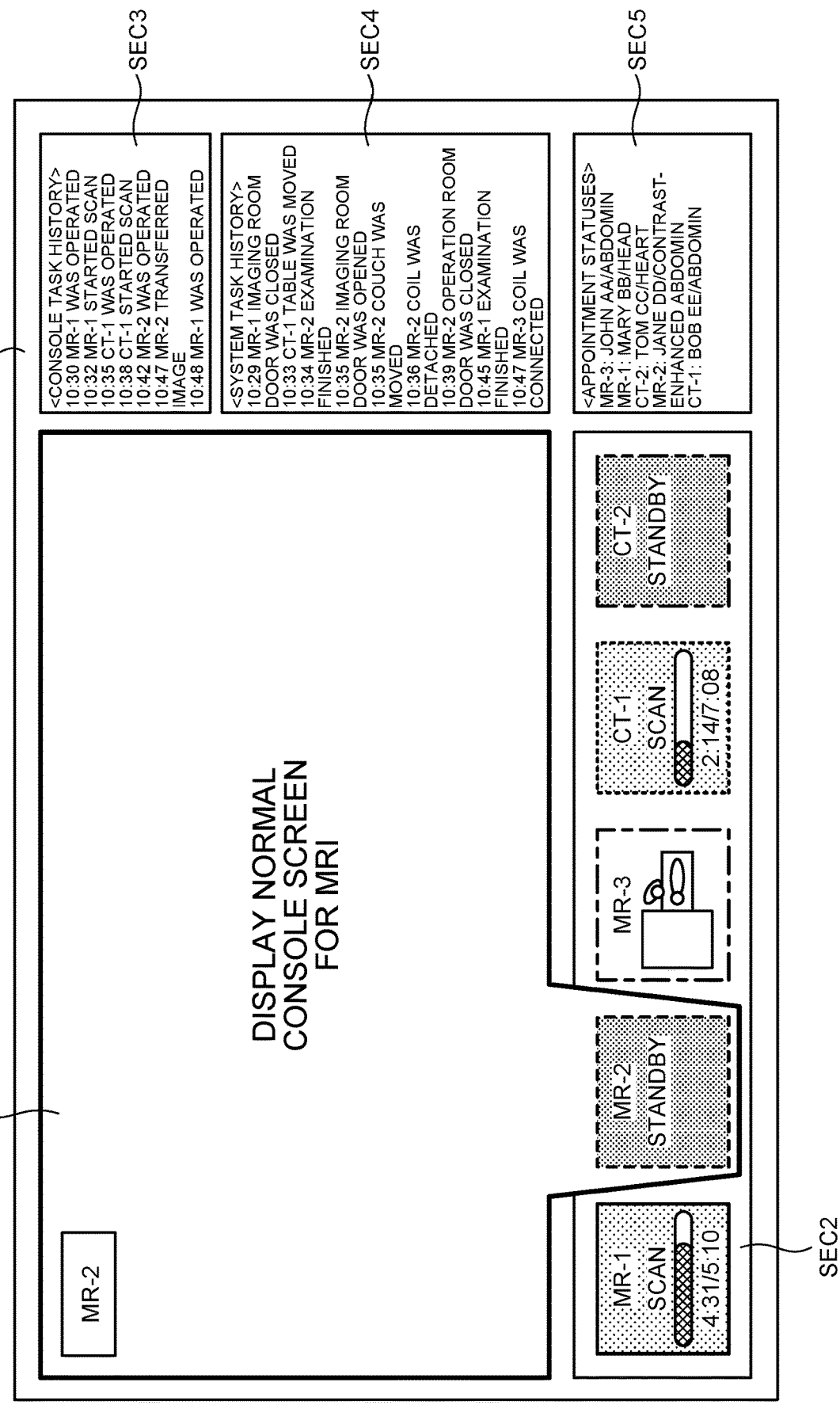
FIG. 6 is a drawing according to the embodiment illustrating an example of a display layout different from that in FIG. 4.

FIG. 6 is a drawing illustrating an example of the display layout different from that in FIG. 4. As illustrated in FIG. 6, the display controlling function 255 displays the status objects in the second section SEC2 as tabs related to the first section SEC1. In FIG. 6, a console screen for the second modality related to the system ID MR-2 is displayed. In this situation, the icon serving as the status object related to the second modality in the second section SEC2 is used as a tab of the first section SEC1. In the display layout in FIG. 6, visibility of the modality operated in the first section SEC1 is enhanced. In a display layout such as that illustrated in FIG. 6, the various types of functions in the first section SEC1 and the second section SEC2 are not lost, while the roles thereof are also independent.

Step S409:

According to a user instruction received via the input interface 240, on the console screen in the first section SEC1, the controlling instruction of settings for image taking conditions and/or image processing operations or the like are input.

Step S410:

When one of the modalities in the second section SEC2 (more specifically, one of the icons corresponding to the status objects) is selected according to a user instruction received via the input interface 240, the display controlling function 255 displays an authentication object in the first section SEC1. For example, in response to an operation performed on the status object related to the second modality 112, the display controlling function 255 displays, in the first section SEC1, the authentication object for causing the input object of the second modality 112 to be displayed in the first section. In response to an operation performed on the authentication object (more specifically, when the button "YES, SWITCH" in the authentication object is pressed via the input interface 240) (step S410: Yes), the process at step S411 will be performed.

On the contrary, when the icons corresponding to the status objects in the second section SEC2 are not selected (step S410: No), the process at step S412 will be performed. Further when the button "NO, DON'T SWITCH" in the authentication object is pressed (step S410: No), the process at step S412 will be performed.

Figure 7:
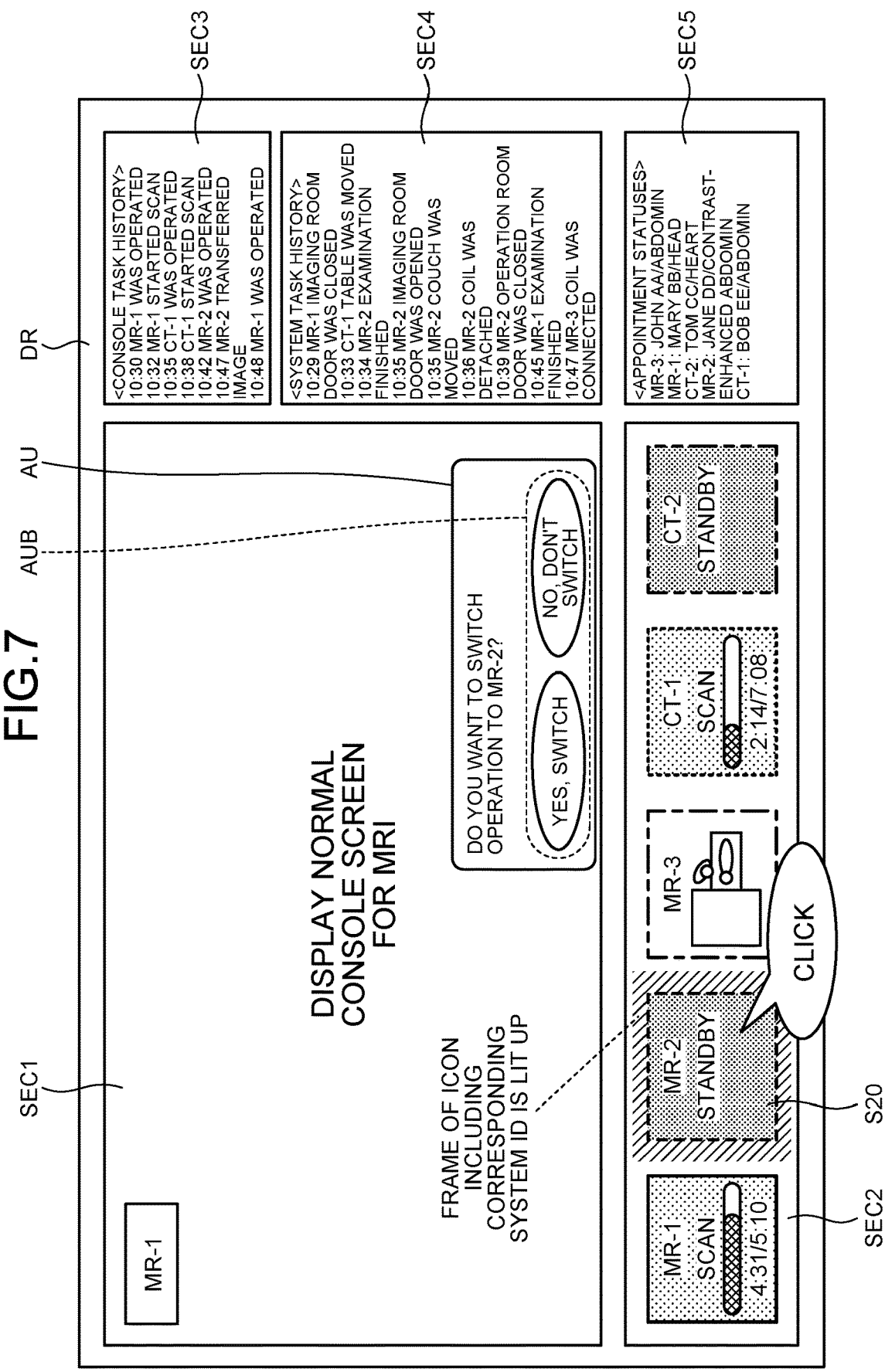
FIG. 7 is a drawing according to the embodiment illustrating an example of an authentication object displayed in the first section.

FIG. 7 is a drawing illustrating an example of an authentication object AU displayed in the first section SEC1, in consideration of the possibility that the operation screen may be switched by an erroneous operation. As illustrated in FIG. 7, in response to pressing (a click) on a status object S2O related to the second modality 112 in the second section SEC2, the display controlling function 255 displays, in the first section SEC1, the authentication object AU including authentication buttons AUB. In this situation, as illustrated in FIG. 7, the display controlling function 255 lights up the surrounding of the frame of the status object S2O being the clicked element. By using the visual effect on the status object S2O being the clicked element, it is possible to enhance visibility of the icon of the second modality 112 related to the status object S2O.

Step S411:

When the authentication button "YES, SWITCH" is pressed in the authentication object AU, the display controlling function 255 displays, in the first section SEC1, the input object related to the selected modality. For example, when the status object S2O related to the second modality 112 having the system ID MR-2 is clicked, and the authentication button AUB "YES, SWITCH" is pressed in the authentication object AU, the display controlling function 255 displays, in the first section SEC1, the input object for inputting an instruction for controlling the second modality 112. After the present step, the processes at step S405 and thereafter are repeatedly performed.

Figure 8:
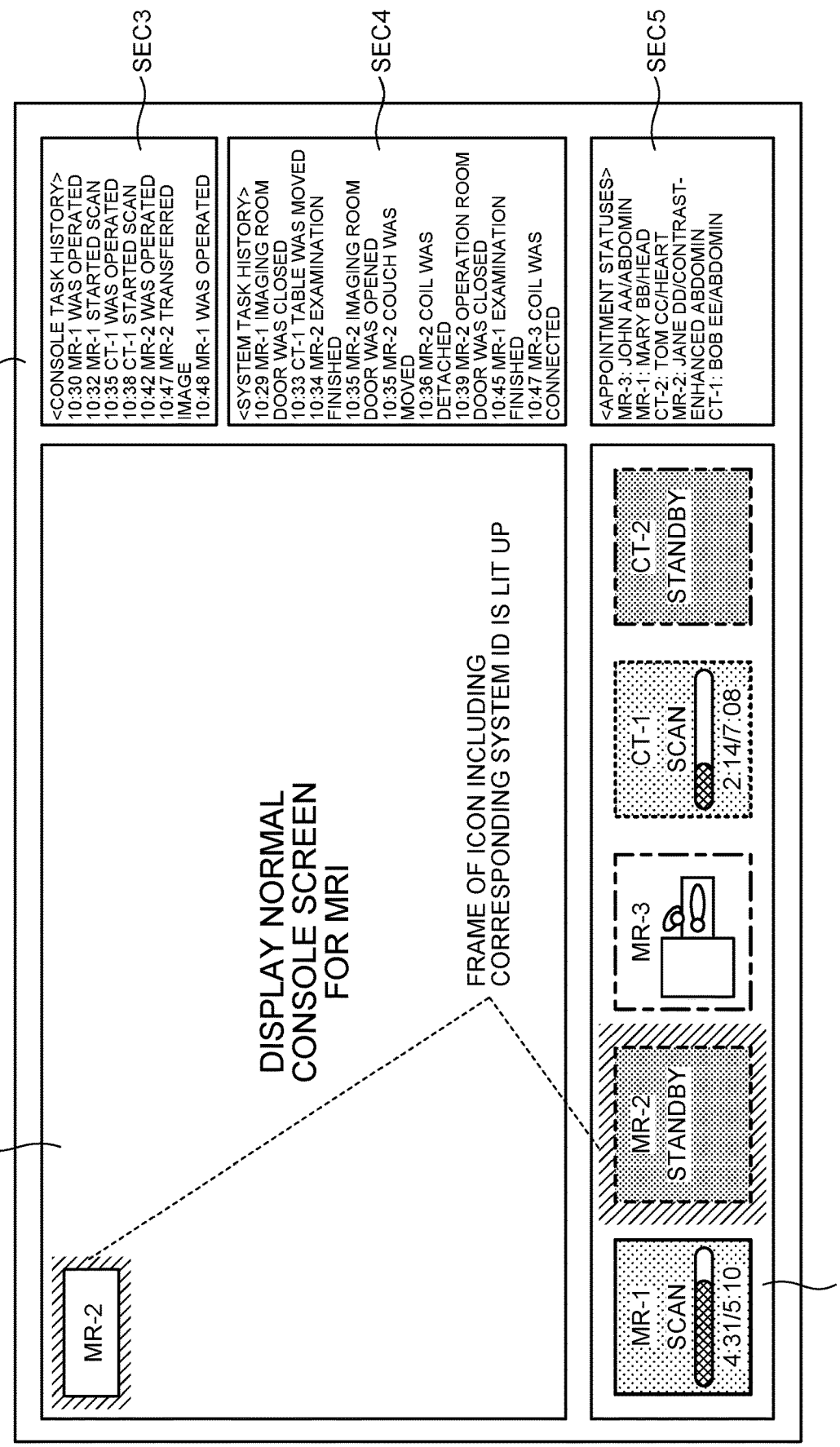
FIG. 8 is a drawing according to the embodiment illustrating an example in which an input object related to a second modality is displayed in the first section in response to an operation performed on the authentication object.

FIG. 8 is a drawing illustrating an example in which the input object related to the second modality 112 is displayed in the first section SEC1, in response to an operation performed on the authentication object AU. In other words, in response to the operation performed on the authentication object AU, the display controlling function 255 displays, in the first section SEC1, the input object for inputting an instruction for controlling the second modality 112, i.e., the input object related to the second modality 112 having the system ID MR-2. In this situation, as illustrated in FIG. 8, in the second section SEC2, the display controlling function 255 may light up the frame of the icon related to the second modality 112 being the target of the operation in the first section SEC1. In addition, as illustrated in FIG. 8, the display controlling function 255 may light up the system ID in the first section SEC1. With these visual effects, the user is able to intuitively recognize the modality currently being operated. The abovementioned visual effects may be kept permanently or may be restrictively used only for a number of seconds after the console screens are switched in the first section SEC1.

Step S412:

When a log-out is input to the modality controlling apparatus 200 according to a user instruction received via the input interface 240 (step S412: Yes), the display controlling process ends. Unless a log-out from the modality controlling apparatus 200 is input (step S412: No), the processes at step S405 and thereafter are repeatedly performed. It should be noted that the process at the present step may be carried out during an arbitrary processing procedure.

On the display 230 configured to display the input object for inputting an instruction for controlling the first modality 111 and the status object indicating the status related to the second modality 112, the modality controlling apparatus 200 according to the embodiment described above is configured to display the input object in the first section SEC1 of the display 230 and to display the status objects in the second section SEC2 of the display 230 which is a section smaller than the first section SEC1. In the present modality controlling apparatus 200, the status denotes at least one of the following: a state of an imaging process performed by at least one of the first modality 111 and the second modality 112; an examination room interior image related to at least one of the first examination room 121 in which the first modality 111 is provided and the second examination room 122 in which the second modality 112 is provided; the environment information of at least one of the first examination room 121 and the second examination room 122; the examined subject information of at least one of a first examined subject imaged by the first modality 111 and a second examined subject imaged by the second modality 112; and the administrators or the workers of the first modality 111 and the second modality 112. With these arrangements, by using the present modality controlling apparatus 200, the user is able to intuitively recognize the modality currently being operated and the various types of statuses of the plurality of modalities.

Further, while the status object has the information indicating the progress in the imaging process performed by the second modality 112, the modality controlling apparatus 200 is configured to change the status object in accordance with the progress. Accordingly, by using the present modality controlling apparatus 200, it is possible to intuitively understand the progress in the imaging process performed by the other modality different from the modality currently being operated.

Further, the modality controlling apparatus 200 according to the embodiment is configured to further display, in the second section SEC2, the status object having the information indicating the progress in the imaging process performed by the first modality 111 and to change the status object having the information indicating the progress in the imaging process by the first modality 111, in accordance with the progress in the imaging process performed by the first modality 111. With these arrangements, by using the present modality controlling apparatus 200, it is possible to intuitively understand the progress in the imaging process performed by the modality currently being operated.

Further, the modality controlling apparatus 200 according to the embodiment is configured to display, in the second section SEC2, the plurality of status objects related to the plurality of modalities including the first modality 111 and the second modality 112 by using the display modes corresponding to the plurality of modalities and is configured to perform at least one of the following: displaying, in the third section SEC3 of the display 230 which is a section smaller than the first section SEC1, the first task history of the tasks performed in the first section SEC1, by using the display modes; displaying, in the fourth section SEC4 of the display 230 which is a section smaller than the first section SEC1, the second task history of the tasks performed in relation to the plurality of modalities, by using the display modes; and displaying, in the fifth section SEC5 of the display 230 which is a section smaller than the first section SEC1, the appointment statuses of the examinations to be performed by the plurality of modalities, by using the display modes. With these arrangements, when the present modality controlling apparatus 200 is used, because the display modes (e.g., the hues) are different among the plurality of modalities, it is possible to easily and intuitively understand the status objects, the first task history, the second task history, and the appointment statuses of the examinations, in relation to the plurality of modalities.

Further, the modality controlling apparatus 200 according to the embodiment is configured, in response to the operation performed on the status object, to display, in the first section SEC1, the authentication object AU for causing the input object of the second modality 112 to be displayed in the first section SEC1 and is configured, in response to the operation performed on the authentication object AU, to display, in the first section SEC1, the input object for inputting an instruction for controlling the second modality 112. With these arrangements, by using the present modality controlling apparatus 200, it is possible to easily and intuitively understand the modality related to the change in the operation.

Further, the modality controlling apparatus 200 according to the embodiment is configured to store the system ID of the first modality 111 so as to be kept in association with the user ID, is configured to store the input object for inputting an instruction for controlling the first modality 111, and is configured, in response to the user's log-in, to display, in the first section SEC1, the input object for inputting an instruction for controlling the first modality 111 associated with the user ID. With these arrangements, because the present modality controlling apparatus 200 is able to display, in the first section SEC1, the input object of the modality corresponding to the administrator, it is possible to improve work efficiency of the administrator.

As explained above, when using the present modality controlling apparatus 200, in the situation where a single user performs parallel processing while using the plurality of modalities, the user is able to easily and intuitively understand, among the plurality of modalities, the status of the modality currently being the target of the operation and the statuses of the other modalities. As a result, by using the present modality controlling apparatus 200, it is possible to prevent the operations on the plurality of modalities from becoming cumbersome and to simplify the workflow. Consequently, by using the present modality controlling apparatus 200, it is possible to reduce burdens on the operator and to enhance operability of the plurality of modalities. It is therefore possible to improve throughput (work efficiency) related to the examinations and the operations on the plurality of modalities.

FIRST APPLICATION EXAMPLE

In the present application example, when an event related to an interruption having high urgency has occurred in a modality while the display controlling process is carried out, the first section SEC1 on the display 230 of the modality controlling apparatus 200 is forcibly switched, and an operation right of the user is also simultaneously switched to the modality experiencing the interruption. Examples of the interruption having high urgency include various types of errors in the modalities and a patient call (or a nurse call) made by the examined subject.

Upon receipt of an interruption command from any of the plurality of modalities, the display controlling function 255 is configured to display, in the first section SEC1, a plurality of pop-up or temporary console screens. Further, when being unable to display the status objects of all the modalities in the second section SEC2 as illustrated in FIG. 5, for example, the display controlling function 255 is configured to cause the second section SEC2 to prioritize the display of the status object related to the modality that issued the interrupting command and the object related to the modality currently performing an imaging process.

In response to receiving an emergency signal output from at least one of the plurality of modalities, the display controlling function 255 is configured to disable operations performed on the input object displayed in the first section SEC1 and to display the event related to the emergency signal in the first section SEC1. For example, in response to receiving an emergency signal from the second modality 112, the display controlling function 255 is configured to disable operations performed on the input object to be used for inputting an instruction for controlling the first modality 111 illustrated in FIGS. 4 to 7 and to further display, in the first section SEC1, the event related to the emergency signal in response to the receipt of the emergency signal.

Further, in response to receiving the emergency signal, the display controlling function 255 is configured to further display, in the first section SEC1, at least one of the following: an input object related to the modality by which the emergency signal was issued; risk information indicating a level of the risk of an event related to the emergency signal; an instruction to eliminate the risk (hereinafter, "risk elimination instruction"); an examination room interior image of the examination room having installed the modality by which the emergency signal was issued; and a contact button to contact a worker in the examination room. For example, in response to receiving an emergency signal from the second modality 112, the display controlling function 255 is configured to further display, in the first section SEC1, at least one of the following: an input object related to the second modality 112; risk information indicating a level of the risk of the event related to the emergency signal; an instruction to eliminate the risk for the second modality 112; an examination room interior image of the second examination room 122 having the second modality 112 installed; and a contact button to contact one or both of a worker and the patient in the second examination room 122.

In the following sections, to explain a specific example, a display controlling process will be explained regarding a situation where, while the first modality 111 having the system ID MR-1 is being operated, an emergency signal is issued from the fourth modality 114 having the system ID CT-1. It is assumed that emergency of the fourth modality 114 is an interruption signal related to occurrence of a system error, which serves as an event related to the emergency signal.

Figure 9:
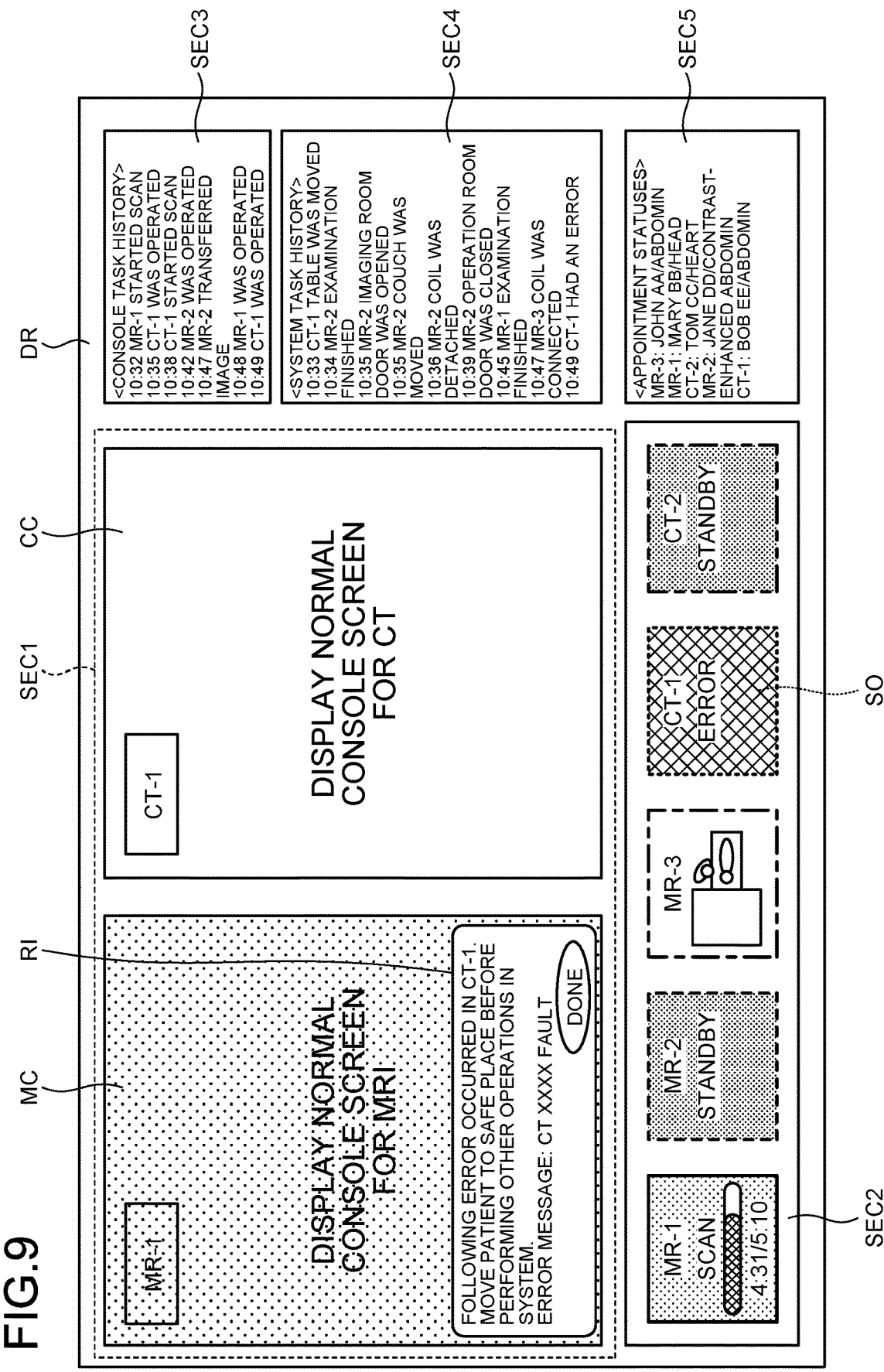
FIG. 9 is a drawing according to a first application example of the embodiment illustrating an example of a display layout displayed on the display upon receipt of an emergency signal related to a system error.

FIG. 9 is a drawing illustrating an example of a display layout displayed on the display 230 upon receipt of the emergency signal related to the system error. As illustrated in FIG. 9, in response to the receipt of the emergency signal, the display controlling function 255 is configured to display, in the first section SEC1, a risk elimination instruction RI as a pop-up, for example, on a console screen MC related to the system ID MR-1 currently being operated. In this situation, the display controlling function 255 is configured to display an error message in the risk elimination instruction RI, as illustrated in FIG. 9. Further, the display controlling function 255 is configured to control the console screen MC so as to temporarily disable user operations on the console screen MC. In this situation, as illustrated in FIG. 9, the display controlling function 255 may change the display mode by, for example, changing the region of the console screen MC into a gray-scale display, so as to help the user intuitively recognize that operations are disabled. As a result, the user is able to intuitively recognize that the console screen MC is currently inoperable.

Further, in response to the receipt of the emergency signal, the display controlling function 255 is configured to display, in the first section SEC1, an input object related to the fourth modality 114 of which the system ID is CT-1, i.e., a console screen CC related to the fourth modality 114. Further, as illustrated in FIG. 9, when the console screen MC currently being operated and the console screen CC of the fourth modality 114 that issued the interruption signal are displayed at the same time, the console screen CC related to the fourth modality 114 is displayed in a region that accounts for 50% or more of the first section SEC1, for example. In the first section SEC1, the display controlling function 255 may display the console screen CC so as to be larger than the console screen MC.

Further, in response to the receipt of the emergency signal, in the first section SEC1, the display controlling function 255 may be configured to further display, in the first section SEC1, an examination room interior image of a fourth examination room 124 having the fourth modality 114 installed, a contact button to contact a worker in the fourth examination room 124, and the risk information. The information that can be displayed in the first section SEC1 in response to the receipt of the emergency signal does not all need to be displayed. It is acceptable to display only necessary information in accordance with the emergency state of the modality. Further, the information to be displayed in the first section SEC1 in response to the receipt of the emergency signal may be set as appropriate by the user's custom preference.

Further, as illustrated in FIG. 9, the display controlling function 255 is configured to display information indicating emergency, in a status object SO of the fourth modality 114 in the second section SEC2. In this situation, as illustrated in FIG. 9, the display controlling function 255 is configured to change the display mode of the status object SO to be in a hue having high visibility.

Figure 10:
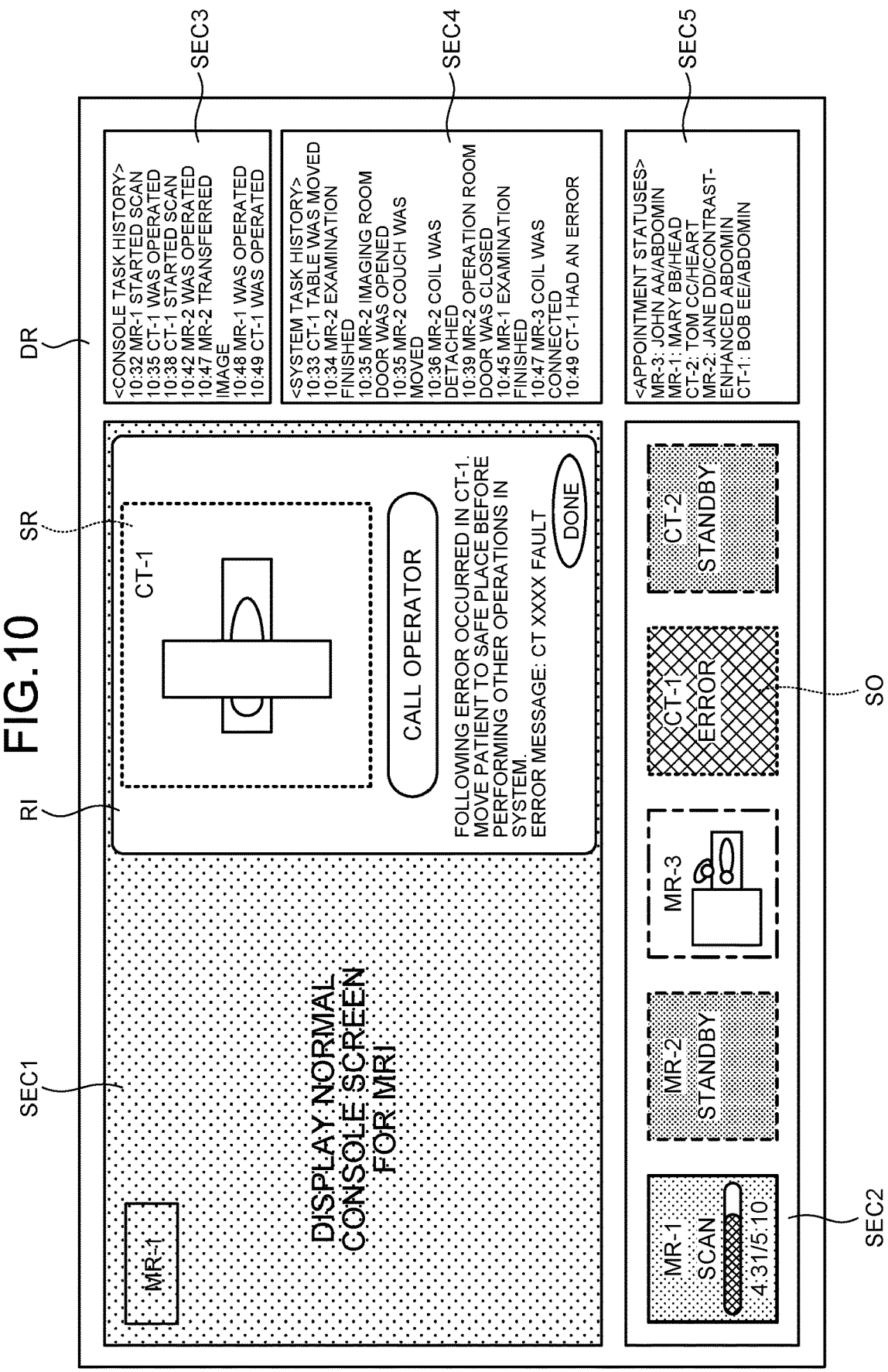
FIG. 10 is another drawing according to the first application example of the embodiment illustrating another example of a display layout displayed on the display upon receipt of the emergency signal related to the system error.

FIG. 10 is another drawing illustrating another example of a display layout displayed on the display 230 upon receipt of the emergency signal related to the system error. Unlike in FIG. 9, in FIG. 10 the first section SEC1 further displays an examination room interior image SR of the fourth examination room 124 having the fourth modality 114 installed and a contact button ("Call Operator") to contact a worker in the fourth examination room 124.

Figure 11:
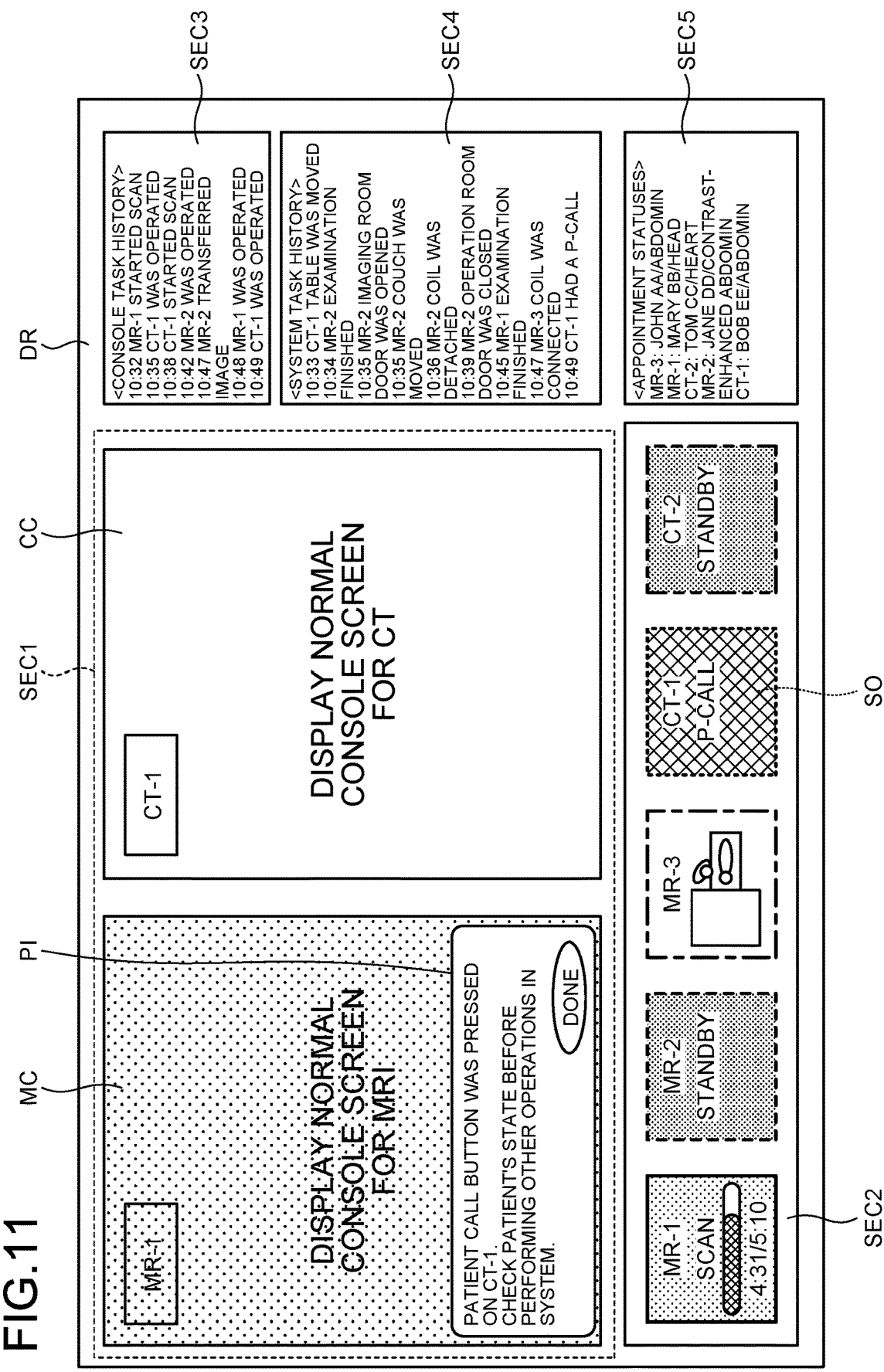
FIG. 11 is yet another drawing according to the first application example of the embodiment illustrating an example of a display layout displayed on the display receipt of an emergency signal related to a patient call.

FIG. 11 is yet another drawing illustrating an example of a display layout displayed on the display 230 upon receipt of an emergency signal related to a patient call. As illustrated in FIG. 11, the display controlling function 255 is configured to display, in the first section SEC1, a risk elimination instruction PI related to a patient call. In this situation, as illustrated in FIG. 11, in the risk elimination instruction PI, the display controlling function 255 is configured to display the system ID of the modality that issued the patient call and a message. Further, the display controlling function 255 is configured to display information indicating the patient call in the status object SO of the fourth modality 114 in the second section SEC2. The rest of the display in the first section SEC1 is the same as that in FIG. 9.

Figure 12:
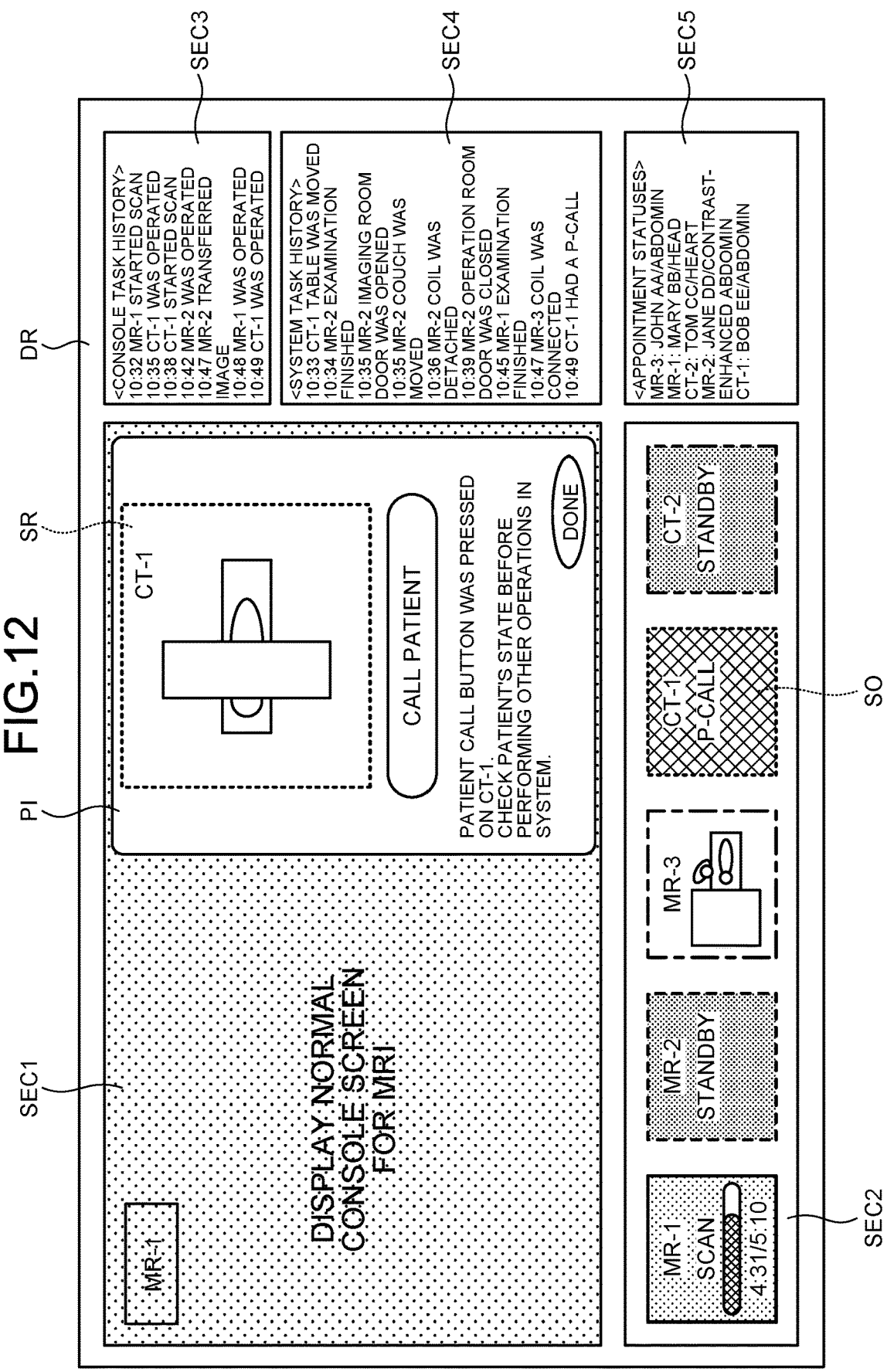
FIG. 12 is yet another drawing according to the first application example of the embodiment illustrating another example of a display layout displayed on the display receipt of the emergency signal related to the patient call.

FIG. 12 is yet another drawing illustrating another example of a display layout displayed on the display 230 upon receipt of the emergency signal related to the patient call. Unlike in FIG. 11, in FIG. 12 the first section SEC1 further displays the examination room interior image SR of the fourth examination room 124 having the fourth modality 114 installed and a contact button ("Call Patient") to contact the patient in the fourth examination room 124.

As illustrated in FIGS. 9 to 12, to make a transition into operations of the first modality 111, it is necessary to solve the abovementioned risky state indicated in FIGS. 9 to 12. After the risky state is avoided, when the button in the pop-up (PI or RI) is pressed by the user via the input interface 240, the display controlling function 255 is configured to cancel the disabled state on the console screen MC related to the first modality 111.

In response to the receipt of the emergency signal related to the emergency of the second modality 112, the modality controlling apparatus 200 according to the first application example of the embodiment described above is configured to disable operations on the input object to be used for inputting an instruction for controlling the first modality 111 and is configured, in response to the receipt of the emergency signal, to display the event related to the emergency signal in the first section SEC1. As a result, by using the modality controlling apparatus 200 according to the present application example, the user is able to easily and intuitively understand the modality that is in an emergency state.

Further, in response to the receipt of the emergency signal, the modality controlling apparatus 200 according to the first application example of the embodiment is configured to further display, in the first section SEC1, at least one of the following: the input object for inputting an instruction for controlling the second modality 112; the risk information indicating the level of the risk of the event related to the emergency signal; the instruction to eliminate the risk for the second modality 112; the examination room interior image of the second examination room 122 in which the second modality 112 is provided; and the contact button for contacting one or both of a worker and the patient in the second examination room 122. As a result, by using the modality controlling apparatus 200 according to the present application example, the user is able to easily and intuitively understand the status of the emergency state regarding the modality in the emergency state.

SECOND APPLICATION EXAMPLE

In the present application example, the user is presented with a recommendation for a modality to be a target of an operation, in accordance with the status of each of the plurality of modalities while the display controlling process is carried out. An example will be explained in which, while an operation is performed on the console screen MC of the first modality 111, the state of the second modality 112 has transitioned into a state (hereinafter, "operable state") requiring a user operation. In that situation, in response to the transition of the second modality 112 into the operable state, the display controlling function 255 is configured to display, in the first section SEC1, an object (hereinafter, "recommendation object") recommending inputting an instruction for controlling the second modality 112.

In other words, when the state of a modality (hereinafter, "operation principal modality") other than the modality currently being operated has transitioned into a status of being principal in operations on the console (being operable for setting image taking conditions, checking an image, performing a post-processing process, etc.), the display controlling function 255 is configured to display, in a region of the first section SEC1 of the display 230, the recommendation object for recommending that an operation right be changed from the currently-operated modality to the operation principle modality. In the following sections, to explain a specific example, it is assumed that the currently-operated modality is the first modality 111, whereas the modality that transitioned into the operable state is the third modality 113 of which the system ID is MR-3.

Figure 13:
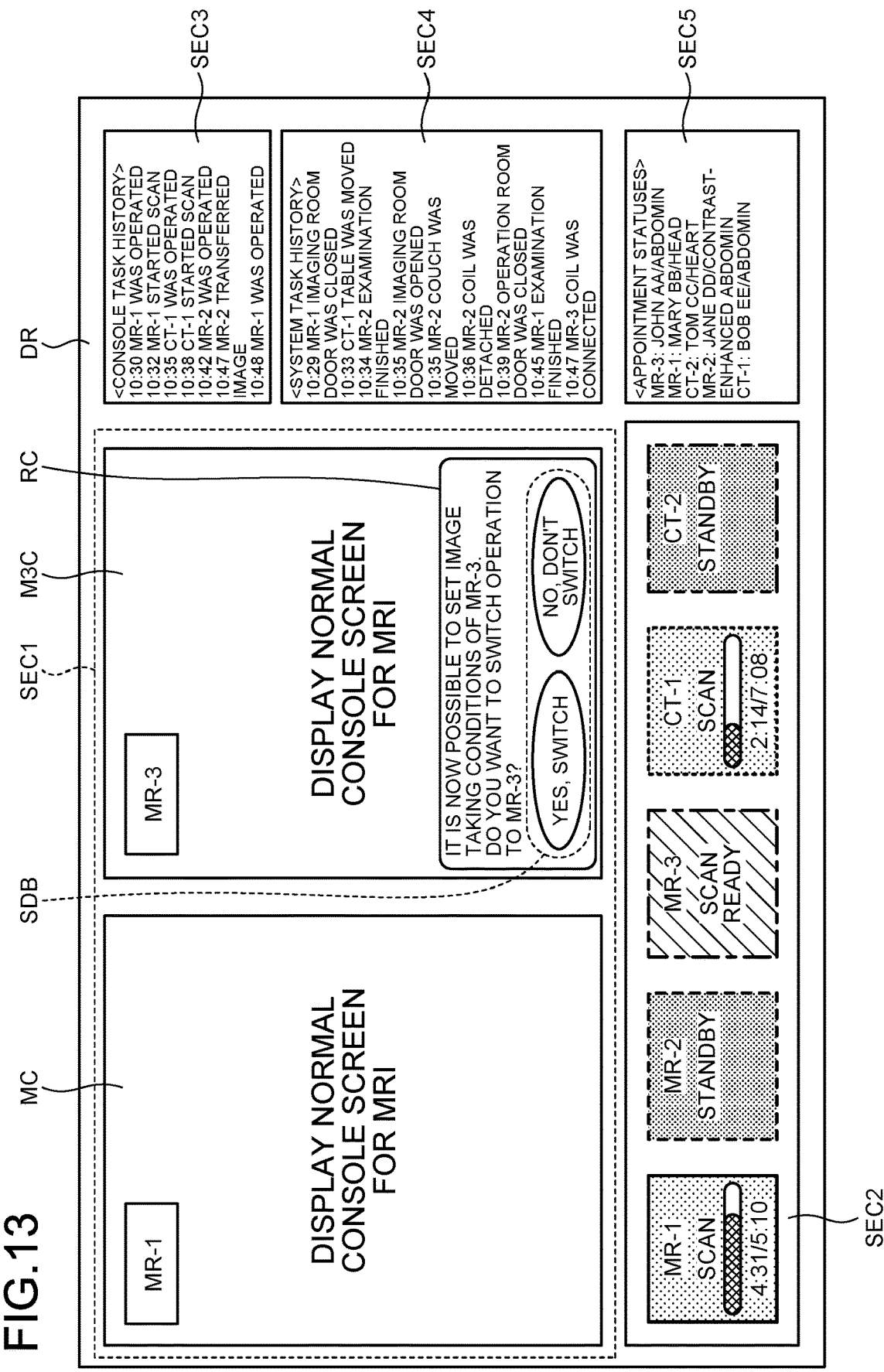
FIG. 13 is a drawing according to a second application example of the embodiment illustrating an example of a display layout displayed on the display when an operation principal modality has transitioned into an operable state.

FIG. 13 is a drawing illustrating an example of a display layout displayed on the display 230 when the operation principal modality has transitioned into the operable state. As illustrated in FIG. 13, in response to receiving the operable state, the display controlling function 255 is configured to display, in the first section DSEC1, an input object related to the third modality (the operation principal modality) 113 of which the system ID is MR-3, i.e., a console screen M3C related to the third modality 113. As illustrated in FIG. 13 when the console screen MC currently being operated and the console screen M3C of the operation principal modality are displayed at the same time, it is preferable to configure the console screen M3C of the operation principal modality to be equal to or smaller than 50% of the first section SEC1, i.e., to have a size equal to or smaller than the currently-operated console screen MC.

In addition, the display controlling function 255 is configured to display, in a console screen RC of the operation principal modality, a recommendation object RC as a pop-up, for example. Further, as illustrated in FIG. 13, the display controlling function 255 is configured to display, within the recommendation object RC, buttons (hereinafter, "switch confirmation buttons") SDB used for determining whether or not switching the modality being a target of the operation is accepted.

Figure 14:
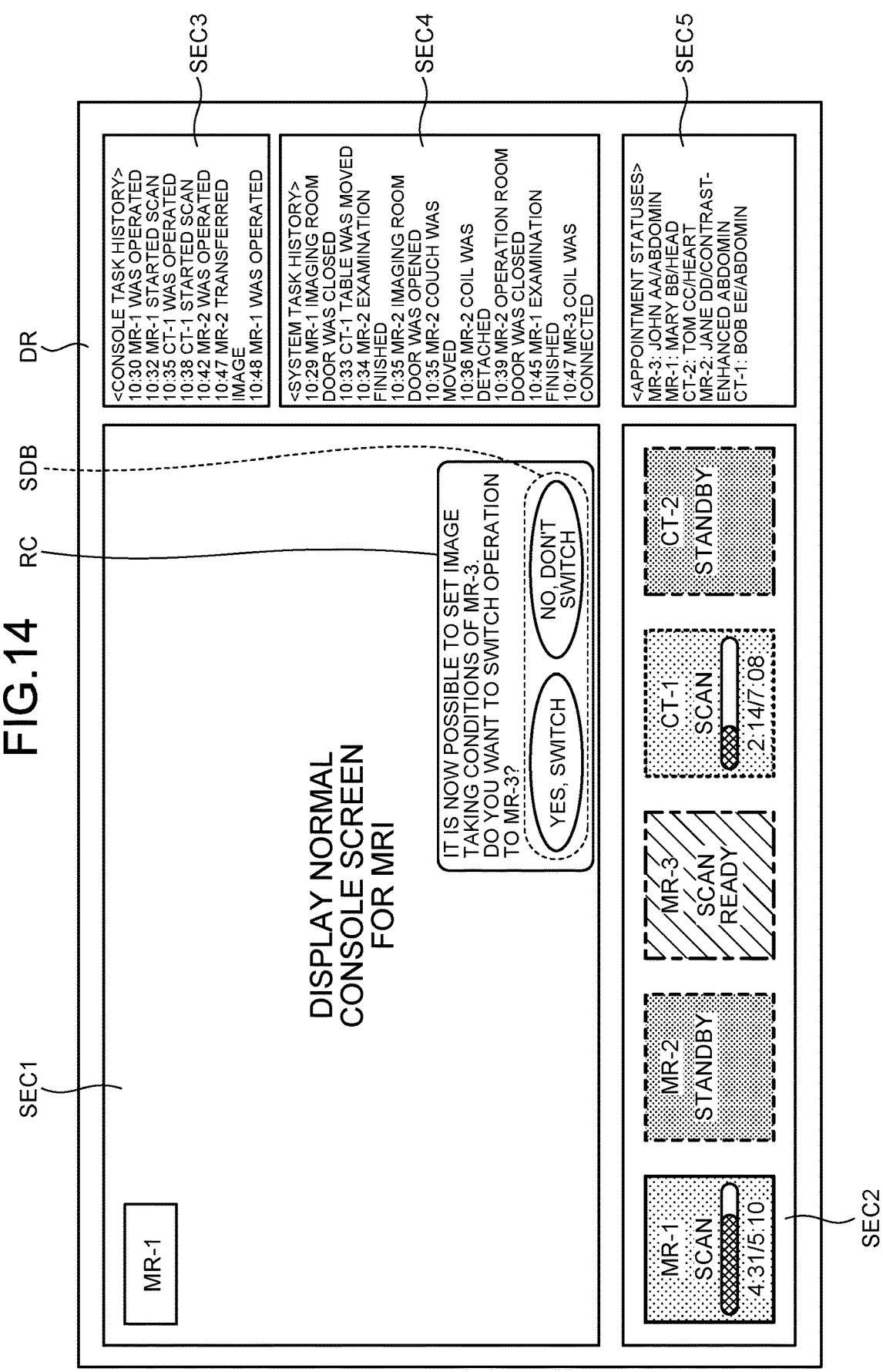
FIG. 14 is another drawing according to the second application example of the embodiment illustrating another example of a display layout displayed on the display the operation principal has transitioned into the operable state.

FIG. 14 is another drawing illustrating another example of a display layout displayed on the display 230 when the operation principal modality has transitioned into the operable state. As illustrated in FIG. 14, in response to receiving the operable state, the display controlling function 255 is configured to display the recommendation object RC in the first section SEC1. The difference from FIG. 13 is that the input object related to the operation principal modality is not displayed in the first section SEC1 in FIG. 14. The rest of the display in the first section SEC1 is the same as that in FIG. 13.

Of the switch confirmation buttons illustrated in FIGS. 13 and 14, when "YES, SWITCH" is pressed, the display controlling function 255 is configured to display, in the first section SEC1, the console screen M3C of the operation principal modality and to close the display of the console screen MC of the first modality 111. As a result, the user becomes able to enter various types of inputs related to the operation principal modality. On the contrary, of the switch confirmation buttons illustrated in FIGS. 13 and 14, when "NO, DON'T SWITCH" is pressed, the display controlling function 255 is configured to close the recommendation object RC in the first section SEC1. In this situation, in FIG. 13, the console screen M3C of the operation principal modality is also closed. In that situation, the user becomes able to continue entering inputs on the console screen that had been operated immediately before the recommendation object RC was displayed.

The modality controlling apparatus 200 according to the second application example of the embodiment described above is configured, in response to the transition of the state of the second modality 112 into the state requiring a user operation, to display, in the first section SEC1, the recommendation object RC recommending inputting an instruction for controlling the second modality 112. As a result, by using the modality controlling apparatus 200 according to the second application example, the user is able to easily and intuitively understand the modality in the operable state. Consequently, by using the present modality controlling apparatus 200, it is possible to efficiently utilize operation time regarding the operations on the modalities. It is therefore possible to improve throughput (work efficiency) related to the examinations and the operations on the plurality of modalities.

THIRD APPLICATION EXAMPLE

In the present application example, when the connection between the modality controlling apparatus 200 and any of the plurality of modalities is disrupted while the display controlling process is carried out, the user is notified of the connection state. The communication interface 210 is configured to wirelessly communicate with each of the plurality of modalities including the first modality 111 and the second modality 112 at predetermined time intervals. The predetermined time intervals may be, for example, 0.1 seconds to a number of seconds.

When the wireless communication between any of the plurality of modalities with the modality controlling apparatus 200 is disrupted for a predetermined time period, the display controlling function 255 is configured to perform at least one of the following: displaying that the wireless communication is disrupted in the first section SEC1; and changing the display mode of the status object of the modality related to the disruption of the wireless communication in the second section SEC2. The predetermined time period may be approximately 10 seconds, for example, for a modality currently performing an imaging process and may be approximately 30 seconds to 1 minutes, for example, for a modality that is not currently performing an imaging process. In other words, the predetermined time period may be changed depending on the status of each of the plurality of modalities. With these arrangements, by checking the wireless communication with each of the plurality of modalities once every predetermined time period, it is possible to notify the user of any communication abnormality with each of the plurality of modalities.

The modality controlling apparatus 200 according to the third application example of the embodiment described above is configured to perform the wireless communication at the predetermined time intervals with each of the plurality of modalities including the first modality 111 and the second modality 112 and is configured, when the wireless communication with any of the plurality of modalities is disrupted for the predetermined time period, to perform at least one of the following: displaying that the wireless communication is disrupted in the first section SEC1; and changing the display mode of the status object of the modality related to the disruption of the wireless communication in the second section SEC2. Consequently, the modality controlling apparatus 200 according to the third application example makes it possible to easily and intuitively understand the modality with which the communication is disrupted.

FOURTH APPLICATION EXAMPLE

In the present application example, when each of the plurality of modalities is controlled by the single modality controlling apparatus 200 and by a single user, an operation prearrangement indicating a plurality of examinations in the order of importance are displayed in another section different from the first to the fifth sections. For example, the display controlling function 255 is configured to display, in a section different from the first section SEC1 and the second section SEC2 or in the second section SEC2, the operation prearrangement in which the plurality of examinations are displayed in the order of importance, on the basis of appointment statuses of the plurality of examinations related to the plurality of modalities including the first modality 111 and the second modality 112 and specifics of each of the plurality of examinations. For example, according to a user instruction received via the input interface 240, the display controlling function 255 is configured to determine a chronological order in which the plurality of examinations are arranged, on the basis of the appointment statuses of the plurality of examinations and the specifics of each of the plurality of examinations.

Figure 15:
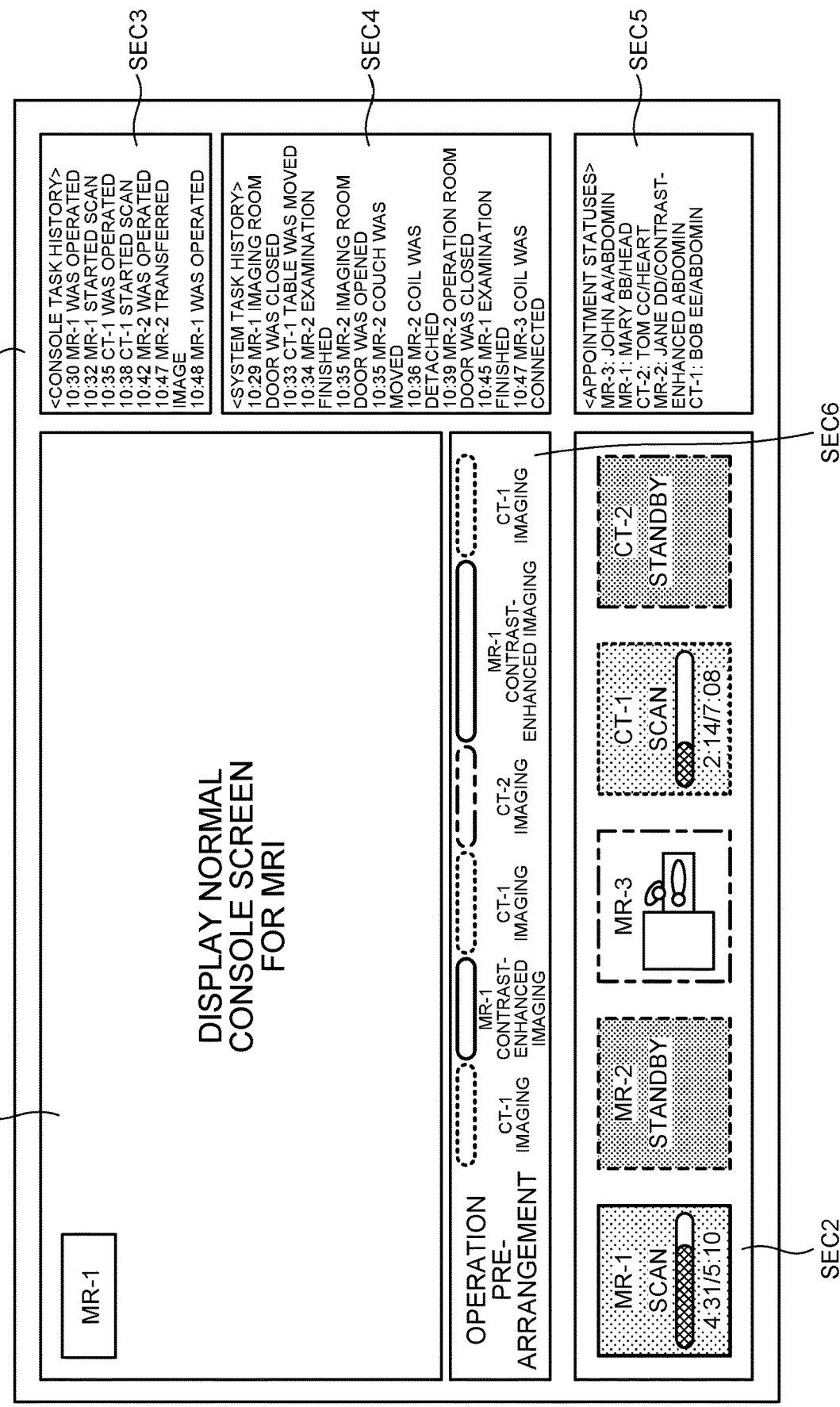
FIG. 15 is a drawing according to a fourth application example of the embodiment illustrating an example of a display layout displaying an operation prearrangement in a sixth section independent of the first to the fifth sections.

FIG. 15 is drawing illustrating an example of a display layout displaying an operation prearrangement in a sixth section SEC6 independent of the first to the fifth sections. As illustrated in FIG. 15, the operation prearrangement indicates, in a time chart, the plurality of examinations (imaging processes) in the order of importance. Alternatively, the operation prearrangement may be displayed in the second section SEC2. Because it is desirable to enable the user to intuitively visually recognize the chronology of the plurality of examinations (imaging processes), it is preferable to configure the sixth section SEC6 to have a belt-like rectangular shape. In this situation, the long sides of the belt-like rectangle may extend along either the long-side direction or the short-side direction of the display 230.

The modality controlling apparatus 200 according to the fourth application example of the embodiment described above is configured to display, in the section different from the first section SEC1 and the second section SEC2 or in the second section SEC2, the operation prearrangement in which the plurality of examinations are displayed in the order of importance on the basis of the appointment statuses of the plurality of examinations related to the plurality of modalities including the first modality 111 and the second modality 112 and the specifics of each of the plurality of examinations. Consequently, by using the modality controlling apparatus 200 according to the fourth application example, the user is able to intuitively visually recognize and understand the chronology of the plurality of examinations (imaging processes). As a result, by using the modality controlling apparatus 200 according to the fourth application example, it is possible to avoid the situation where, for example, processes are simultaneously performed for a contrast-enhanced imaging process using an MRI apparatus and for an imaging process involving a radiation emission from an X-ray CT apparatus, an X-ray diagnosis apparatus, or the like. Consequently, the modality controlling apparatus 200 according to the fourth application example makes it possible to avoid the situation where processes related to important operations run parallel to each other. It is therefore possible to reduce the possibility where the user's processing capabilities are surpassed at the time of emergency.

When the technical concept of the embodiments and the like is realized by using a display controlling program, the display controlling program causes the computer to realize: displaying, in the first section SEC1 of the display 230, the input object for inputting an instruction for controlling the first modality 111; and displaying, in the second section SEC2 of the display 230 which is a section smaller than the first section SEC1, the status object indicating the status related to the second modality 112. Because the processing procedure and advantageous effects of the display controlling program are the same as those of the embodiments, explanations thereof will be omitted.

According to at least one aspect of the embodiments and the like described above, it is possible to enhance operability related to the inputs for controlling the plurality of modalities.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A modality controlling apparatus, comprising:
   a display configured to display an input object for inputting an instruction for controlling one of a plurality of first modalities and a status object indicating a status related to a second modality; and
   processing circuitry configured to display the input object in a first section of the display and to display the status object in a second section of the display, which is a section smaller than the first section,
   wherein in response to a user log-in, the processing circuitry is further configured to display the input object in the first section of the display to allow the user to input an instruction for controlling a particular first modality, which is one of a first modality associated with an ID of the user, a first modality positioned closest to the modality controlling apparatus and a first modality that was operated by the modality controlling apparatus before a log-out from the modality controlling apparatus.

2. The modality controlling apparatus according to claim 1, wherein
   the status object includes information indicating progress in an imaging process performed by the second modality, and
   the processing circuitry is further configured to change the status object in accordance with the progress.

3. The modality controlling apparatus according to claim 1, wherein
   the processing circuitry is further configured to display, in the second section, a status object including information indicating progress in an imaging process performed by the particular first modality, and
   in accordance with the progress in the imaging process performed by the particular first modality, the processing circuitry is further configured to change the status object having the information indicating the progress in the imaging process performed by the particular first modality.

4. The modality controlling apparatus according to claim 3, wherein the status denotes at least one of: a state of an imaging process performed by at least one of the particular first modality and the second modality, an examination room interior image related to at least one of a first examination room in which the particular first modality is provided and a second examination room in which the second modality is provided, environment information in at least one of the first examination room and the second examination room, examined subject information of at least one of a first examined subject imaged by the particular first modality and a second examined subject imaged by the second modality, and administrators or workers of the particular first modality and the second modality.

5. The modality controlling apparatus according to claim 1, wherein
   the processing circuitry is further configured to display, in the second section, a plurality of status objects indicating statuses related to a plurality of modalities including the particular first modality and the second modality, by using a display mode corresponding to the plurality of modalities, and
   the processing circuitry is further configured to perform at least one of: displaying, in a third section of the display which is a section smaller than the first section, a first task history of tasks performed in the first section, while using the display mode, displaying, in a fourth section of the display which is a section smaller than the first section, a second task history of tasks performed in relation to the plurality of modalities, while using the display mode, and displaying, in a fifth section of the display which is a section smaller than the first section, appointment statuses of examinations to be performed by the plurality of modalities, while using the display mode.

6. The modality controlling apparatus according to claim 1, wherein
   in response to an operation performed on the status object, the processing circuitry is further configured to display, in the first section, an authentication object for causing an input object of the second modality to be displayed in the first section, and
   in response to an operation performed on the authentication object, the processing circuitry is further configured to display, in the first section, the input object for inputting an instruction for controlling the second modality.

7. The modality controlling apparatus according to claim 1, further comprising:

a memory configured to store therein a system ID of the first modality associated with the ID of the user so as to be kept in association with the ID of the user, and to store therein the input object for inputting the instruction for controlling the first modality, wherein in response to the user logging in, the processing circuitry is further configured to display, in the first section, the input object for inputting the instruction for controlling the first modality associated with the ID of the user.

8. The modality controlling apparatus according to claim 1, wherein
in response to receiving an emergency signal from the second modality, the processing circuitry is further configured to disable operations performed on the input object used for inputting the instruction for controlling the particular first modality, and
in response to the receiving of the emergency signal, the processing circuitry is further configured to display an event related to the emergency signal in the first section.

9. The modality controlling apparatus according to claim 8, wherein, in response to the receiving of the emergency signal, the processing circuitry is further configured to further display, in the first section, at least one of: an input object for inputting an instruction for controlling the second modality, risk information indicating a level of a risk of the event, an instruction to eliminate the risk for the second modality, an examination room interior image of a second examination room in which the second modality is provided; or a contact button for contacting one or both of a worker and an examined subject in the second examination room.

10. The modality controlling apparatus according to claim 1, wherein, in response to a state of the second modality having transitioned into a state requiring a user operation, the processing circuitry is further configured to display, in the first section, a recommendation object that recommends inputting an instruction for controlling the second modality.

11. The modality controlling apparatus according to claim 1, further comprising:
a communication interface configured to wirelessly communicate with each of a plurality of modalities including the particular first modality and the second modality, at predetermined time intervals, wherein
when the wireless communication with any of the plurality of modalities is disrupted for a predetermined time period, the processing circuitry is further configured to perform at least one of: displaying that the wireless communication is disrupted in the first section, and changing, in the second section, a display mode of the status object of any of the modalities related to the disruption of the wireless communication.

12. The modality controlling apparatus according to claim 1, wherein, based on appointment statuses of a plurality of examinations related to a plurality of modalities including the particular first modality and the second modality and specifics of each of the plurality of examinations, the processing circuitry is further configured to display, in another section different from the first section and the second section or in the second section, an operation prearrangement indicating the plurality of examinations in order of importance.

13. A non-transitory computer-readable storage medium storing therein a display controlling program that causes a computer to perform a method comprising:
displaying, in a first section of a display, an input object for inputting an instruction for controlling one of a plurality of first modalities; and
displaying, in a second section of the display which is a section smaller than the first section, a status object indicating a status related to a second modality,
wherein the step of displaying the input object comprises, in response to a user log-in, displaying the input object in the first section of the display to allow the user to input an instruction for controlling a particular first modality, which is one of a first modality associated with an ID of the user, a first modality positioned closest to the modality controlling apparatus, and a first modality that was operated by the modality controlling apparatus before a log-out from the modality controlling apparatus.

14. A modality controlling apparatus, comprising:
a display configured to display an input object for inputting an instruction for controlling one of a plurality of first modalities and a status object indicating a status related to a second modality; and
processing circuitry configured to display the input object in a first section of the display and to display the status object in a second section of the display, which is a section smaller than the first section,
wherein, in response to a state of the second modality having transitioned into a state requiring a user operation, the processing circuitry is further configured to display, in the first section, a recommendation object that recommends inputting an instruction for controlling the second modality.

* * * * *